US012685628B2

(12) United States Patent
Sostek

(10) Patent No.: US 12,685,628 B2
(45) Date of Patent: Jul. 21, 2026

(54) SYNTHETIC SCAFFOLDS

(71) Applicant: Biostage, Inc, Holliston, MA (US)

(72) Inventor: Ron Sostek, Newton, MA (US)

(73) Assignee: HARVARD APPARATUS REGENERATIVE TECHNOLOGY, INC., Holliston, MA (US)

( * ) Notice: Subject to any disclaimer, the term of this patent is extended or adjusted under 35 U.S.C. 154(b) by 0 days.

(21) Appl. No.: 17/674,736

(22) Filed: Feb. 17, 2022

(65) Prior Publication Data

US 2022/0168089 A1 Jun. 2, 2022

Related U.S. Application Data

(62) Division of application No. 14/760,014, filed as application No. PCT/US2014/010941 on Jan. 9, 2014, now Pat. No. 11,284,987.

(60) Provisional application No. 61/769,725, filed on Feb. 26, 2013, provisional application No. 61/750,788, filed on Jan. 9, 2013.

(51) Int. Cl.
| *A61F 2/02* | (2006.01) |
| *A61F 2/06* | (2013.01) |
| *A61L 27/48* | (2006.01) |
| *A61L 27/56* | (2006.01) |

(52) U.S. Cl.
CPC ................ *A61F 2/02* (2013.01); *A61L 27/48* (2013.01); *A61L 27/56* (2013.01)

(58) Field of Classification Search
CPC ........ A61F 2/02; A61F 2/04; A61F 2002/043; A61F 2/022; A61F 2/06; A61F 2/062
See application file for complete search history.

(56) References Cited

U.S. PATENT DOCUMENTS

| 5,032,508 A | 7/1991 | Naughton et al. |
| 5,160,490 A | 11/1992 | Naughton et al. |
| (Continued) | | |

FOREIGN PATENT DOCUMENTS

| EP | 610423 A1 | 8/1994 |
| WO | 99/47922 A2 | 9/1999 |
| (Continued) | | |

OTHER PUBLICATIONS

Bouffi et al., The role of pharmacologically active microcarriers releasing TGF-beta3 in cartilage formation in vivo by mesenchymal stem cells. Biomaterials. Sep. 2010;31(25):6485-93. doi: 10.1016/j.biomaterials.2010.05.013. Epub Jun. 8, 2010.

(Continued)

*Primary Examiner* — Seema Mathew

(57) ABSTRACT

Aspects of this disclosure relate to a combination of techniques and/or materials that can be used to form a synthetic scaffold for solid and/or hollow organs or tissue. In some embodiments, methods are provided that involve assembling a synthetic scaffold using a first material for a first structural component and a second material for a second structural component, in which the first or second structural component in a perfusion pathway. In some embodiments, materials (e.g. synthetic materials) for the scaffold are printed, molded, cast, polymerized or electrospun. In some embodiments, a scaffold may mimic a natural scaffold or several features of a natural scaffold.

5 Claims, 9 Drawing Sheets

(56) References Cited

U.S. PATENT DOCUMENTS

| | | | |
|---|---|---|---|
| 5,266,480 A | 11/1993 | Naughton et al. | |
| 5,399,665 A * | 3/1995 | Barrera | C12N 5/0068 |
| | | | 435/182 |
| 5,433,909 A | 7/1995 | Martakos et al. | |
| 5,443,950 A | 8/1995 | Naughton et al. | |
| 5,478,739 A | 12/1995 | Slivka et al. | |
| 5,512,475 A | 4/1996 | Naughton et al. | |
| 5,514,378 A | 5/1996 | Mikos et al. | |
| 5,516,680 A | 5/1996 | Naughton et al. | |
| 5,516,681 A | 5/1996 | Naughton et al. | |
| 5,518,915 A | 5/1996 | Naughton et al. | |
| 5,541,107 A | 7/1996 | Naughton et al. | |
| 5,578,485 A | 11/1996 | Naughton et al. | |
| 5,602,026 A | 2/1997 | Dunn et al. | |
| 5,624,840 A | 4/1997 | Naughton et al. | |
| 5,677,355 A | 10/1997 | Shalaby et al. | |
| 5,759,830 A | 6/1998 | Vacanti et al. | |
| 5,770,193 A | 6/1998 | Vacanti et al. | |
| 5,770,417 A | 6/1998 | Vacanti et al. | |
| 5,785,964 A | 7/1998 | Naughton et al. | |
| 5,792,603 A | 8/1998 | Dunkelman et al. | |
| 5,800,537 A | 9/1998 | Bell | |
| 5,855,610 A | 1/1999 | Vacanti et al. | |
| 5,858,721 A | 1/1999 | Naughton et al. | |
| 5,863,531 A | 1/1999 | Naughton et al. | |
| 5,902,741 A | 5/1999 | Purchio et al. | |
| 5,916,265 A | 6/1999 | Hu | |
| 5,928,945 A | 7/1999 | Seliktar et al. | |
| 6,008,049 A | 12/1999 | Naughton et al. | |
| 6,022,743 A | 2/2000 | Naughton et al. | |
| 6,087,552 A | 7/2000 | Gregory | |
| 6,140,039 A | 10/2000 | Naughton et al. | |
| 6,372,495 B1 | 4/2002 | Flendrig | |
| 6,376,244 B1 | 4/2002 | Atala | |
| 6,379,956 B1 | 4/2002 | Bader | |
| 6,416,995 B1 | 7/2002 | Wolfinbarger | |
| 6,428,802 B1 | 8/2002 | Atala | |
| 6,537,567 B1 | 3/2003 | Niklason et al. | |
| 6,960,427 B2 | 11/2005 | Haverich et al. | |
| 6,962,814 B2 | 11/2005 | Mitchell et al. | |
| 7,244,272 B2 * | 7/2007 | Dubson | D04H 3/073 |
| | | | 623/1.42 |
| 7,316,822 B2 | 1/2008 | Binette et al. | |
| 7,371,400 B2 | 5/2008 | Borenstein et al. | |
| 7,531,503 B2 | 5/2009 | Atala et al. | |
| 7,662,409 B2 | 2/2010 | Masters | |
| 7,829,108 B2 | 11/2010 | Van Dyke et al. | |
| 7,947,069 B2 * | 5/2011 | Sanders | B32B 5/02 |
| | | | 623/1.1 |
| 8,057,535 B2 | 11/2011 | Hashi et al. | |
| 8,221,777 B2 | 7/2012 | Van Dyke et al. | |
| 8,470,520 B2 | 6/2013 | Ott et al. | |
| 8,507,263 B2 | 8/2013 | Asnaghi et al. | |
| 9,040,921 B2 | 5/2015 | Sostek | |
| 9,918,463 B2 * | 3/2018 | Zink | A01N 1/143 |
| 11,284,987 B2 * | 3/2022 | Sostek | A61F 2/02 |
| 2002/0115208 A1 | 8/2002 | Mitchell et al. | |
| 2002/0172705 A1 | 11/2002 | Murphy et al. | |
| 2002/0182241 A1 | 12/2002 | Borenstein et al. | |
| 2002/0182261 A1 | 12/2002 | Dai et al. | |
| 2003/0021827 A1 | 1/2003 | Malaviya et al. | |
| 2003/0087428 A1 | 5/2003 | Wolfinbarger et al. | |
| 2003/0100108 A1 | 5/2003 | Altman et al. | |
| 2003/0100944 A1 * | 5/2003 | Laksin | D04H 1/728 |
| | | | 623/1.44 |
| 2003/0124099 A1 | 7/2003 | Atala | |
| 2003/0129736 A1 | 7/2003 | Mitrani | |
| 2003/0129751 A1 | 7/2003 | Grikscheit et al. | |
| 2003/0166274 A1 | 9/2003 | Hewitt et al. | |
| 2003/0168403 A1 * | 9/2003 | Corcho-Sanchez | C12M 29/04 |
| | | | 210/631 |
| 2003/0171053 A1 * | 9/2003 | Sanders | B32B 5/02 |
| | | | 442/341 |
| 2004/0044403 A1 | 3/2004 | Bischoff et al. | |

| | | | |
|---|---|---|---|
| 2004/0058440 A1 | 3/2004 | Brown et al. | |
| 2004/0110285 A1 | 6/2004 | Lendlein et al. | |
| 2005/0003535 A1 * | 1/2005 | Gerlach | C12M 21/08 |
| | | | 435/1.1 |
| 2005/0009178 A1 | 1/2005 | Yost et al. | |
| 2005/0013870 A1 | 1/2005 | Freyman et al. | |
| 2005/0107868 A1 | 5/2005 | Nakayama et al. | |
| 2005/0137675 A1 | 6/2005 | Dubson et al. | |
| 2005/0196423 A1 | 9/2005 | Batich et al. | |
| 2005/0203636 A1 | 9/2005 | McFetridge | |
| 2005/0209687 A1 | 9/2005 | Sitzmann et al. | |
| 2005/0256588 A1 | 11/2005 | Sawa et al. | |
| 2006/0035376 A1 | 2/2006 | Geltser | |
| 2006/0084759 A1 | 4/2006 | Calabro et al. | |
| 2006/0085063 A1 | 4/2006 | Shastri et al. | |
| 2006/0141012 A1 | 6/2006 | Gingras | |
| 2006/0154361 A1 * | 7/2006 | Wikswo | C12M 23/16 |
| | | | 435/297.5 |
| 2006/0204441 A1 | 9/2006 | Atala et al. | |
| 2006/0204445 A1 | 9/2006 | Atala et al. | |
| 2006/0204539 A1 | 9/2006 | Atala et al. | |
| 2006/0239981 A1 | 10/2006 | Yoo et al. | |
| 2006/0240061 A1 | 10/2006 | Atala et al. | |
| 2006/0253192 A1 | 11/2006 | Atala et al. | |
| 2006/0257377 A1 | 11/2006 | Atala et al. | |
| 2006/0258004 A1 | 11/2006 | Kosnik et al. | |
| 2007/0005139 A1 | 1/2007 | Vacanti et al. | |
| 2007/0059293 A1 | 3/2007 | Atala | |
| 2008/0112995 A1 | 5/2008 | Shalev | |
| 2008/0131473 A1 | 6/2008 | Brown et al. | |
| 2008/0145920 A1 * | 6/2008 | Bouten | C12M 29/10 |
| | | | 435/284.1 |
| 2008/0260831 A1 | 10/2008 | Badylak et al. | |
| 2008/0292677 A1 | 11/2008 | Cortiella et al. | |
| 2009/0035855 A1 | 2/2009 | Mng et al. | |
| 2009/0060961 A1 | 3/2009 | Naruse et al. | |
| 2009/0075382 A1 | 3/2009 | Sachlos | |
| 2009/0088828 A1 * | 4/2009 | Shalev | D01D 5/0084 |
| | | | 623/1.2 |
| 2009/0142836 A1 | 6/2009 | Wang et al. | |
| 2009/0265005 A1 | 10/2009 | Yoo et al. | |
| 2010/0034791 A1 | 2/2010 | Lelkes et al. | |
| 2010/0061962 A1 | 3/2010 | Li | |
| 2010/0093066 A1 | 4/2010 | Taylor et al. | |
| 2010/0129450 A1 | 5/2010 | Atala et al. | |
| 2010/0148404 A1 | 6/2010 | Smida et al. | |
| 2010/0221304 A1 | 9/2010 | Tan et al. | |
| 2010/0233115 A1 | 9/2010 | Patel et al. | |
| 2010/0292791 A1 | 11/2010 | Lu et al. | |
| 2011/0033918 A1 | 2/2011 | Asnaghi et al. | |
| 2011/0046732 A1 | 2/2011 | Dyke et al. | |
| 2011/0224800 A1 | 9/2011 | Ludlow et al. | |
| 2011/0250688 A1 | 10/2011 | Hasan | |
| 2012/0068384 A1 | 3/2012 | Phaneuf et al. | |
| 2012/0135234 A1 | 5/2012 | Netravali et al. | |
| 2012/0183944 A1 | 7/2012 | Taylor et al. | |
| 2012/0259415 A1 | 10/2012 | Van Dyke et al. | |
| 2012/0271405 A1 | 10/2012 | Soletti et al. | |
| 2012/0330437 A1 | 12/2012 | El-Kurdi et al. | |
| 2013/0030548 A1 | 1/2013 | Ling | |
| 2013/0041265 A1 | 2/2013 | Sostek et al. | |
| 2013/0109088 A1 | 5/2013 | Ott et al. | |
| 2013/0177972 A1 | 7/2013 | Green et al. | |
| 2013/0204288 A1 | 8/2013 | Johnson et al. | |
| 2013/0236879 A1 | 9/2013 | Berry et al. | |
| 2013/0251687 A1 | 9/2013 | Christman et al. | |
| 2014/0107803 A1 | 4/2014 | Grosse | |
| 2014/0124670 A1 | 5/2014 | Sostek | |
| 2014/0141152 A1 * | 5/2014 | Sostek | D04H 1/43838 |
| | | | 427/2.24 |
| 2014/0141552 A1 | 5/2014 | Zou et al. | |
| 2014/0377848 A1 | 12/2014 | Zink et al. | |
| 2014/0377863 A1 | 12/2014 | Seifalain et al. | |
| 2015/0011892 A1 | 1/2015 | Sostek | |
| 2015/0064142 A1 * | 3/2015 | Green | A61L 27/56 |
| | | | 623/23.72 |
| 2015/0342719 A1 * | 12/2015 | Chen | B01D 69/08 |
| | | | 428/221 |

(56)          References Cited

U.S. PATENT DOCUMENTS

| | | | | |
|---|---|---|---|---|
| 2015/0359621 A1* | 12/2015 | Sostek | ................... | A61L 27/56 |
| | | | | 623/23.72 |
| 2016/0030637 A1* | 2/2016 | Ross | ................... | A61L 27/3633 |
| | | | | 435/395 |
| 2024/0033066 A1* | 2/2024 | Fodor | ................. | A61L 27/3834 |

FOREIGN PATENT DOCUMENTS

| | | | |
|---|---|---|---|
| WO | 2000/59618 A1 | 10/2000 |
| WO | 03087292 A2 | 10/2003 |
| WO | 2005/063316 A1 | 7/2005 |
| WO | 2006/087101 A1 | 8/2006 |
| WO | 2006/099315 A2 | 9/2006 |
| WO | 2006/099332 A2 | 9/2006 |
| WO | 2006/099333 A2 | 9/2006 |
| WO | 2006/099334 A2 | 9/2006 |
| WO | 2006/099372 A2 | 9/2006 |
| WO | 2006/099373 A2 | 9/2006 |
| WO | 2007/025233 A1 | 3/2007 |
| WO | 2007/124127 A2 | 11/2007 |
| WO | 2008/100534 A2 | 8/2008 |
| WO | 20 11/062621 A2 | 5/2011 |
| WO | 2012/031162 A1 | 3/2012 |
| WO | 2012/080390 A1 | 6/2012 |
| WO | 2013155488 A2 | 10/2013 |

OTHER PUBLICATIONS

Chen et al., Formation of lung alveolar-like structures in collagen-glycosaminoglycan scaffolds in vitro. Tissue Eng. Sep.-Oct. 2005; 11(9-10): 1436-48.

Cortiella et al., Tissue-engineered lung: an in vivo and in vitro comparison of polyglycolic acid and pluronic F-127 hydrogel/somatic lung progenitor cell constructs to support tissue growth. Tissue Eng. May 2006;l2(5):1213-25.

De Mel et al., In situ endothelialization potential of a biofunctionalised nanocomposite biomaterial-based small diameter bypass graft. Biomed Mater Eng. 2009;19(4-5):317-31. doi: 10.3233/BME-2009-0597.

Doshi et al., Electrospinning process and applications of electrospun fibers. J Electrostat. Aug. 1995;35(2-3):151-60. Selected papers from 1993 IEEE Industry Applications Society Meeting "Electrostatics in Polymer Processing and Charge Monitoring.".

Hoganson et al., Tissue engineering and organ structure: a vascularized approach to liver and lung. Pediatr Res. May 2008;63(5):520-6. doi: 10.1203/0l.pdr.0000305879.38476.0c.

Ingenito et al., Design and testing of biological scaffolds for delivering reparative cells to target sites in the lung. J Tissue Eng Regen Med. Jun. 2010;4(4):259-72. doi: 10.1002/term.237.

Kannan et al., Silsesquioxane nanocomposites as tissue implants. Plast Reconstr Surg. May 2007;ll9(6):1653-62.

Kannan et al., The antithrombogenic potential of a polyhedral oligomeric silsesquioxane (POSS) nanocomposite. Biomacromolecules. Jan. 2006;7(1):215-23. Epub Nov. 15, 2005.

Kannan et al., The endothelialization of polyhedral oligomeric silsesquioxane nanocomposites: an in vitro study. Cell Biochem Biophys. 2006;45(2):129-36.

Kidane et al., A novel nanocomposite polymer for development of synthetic heart valve leaflets. Acta Biomater. Sep. 2009;5(7):2409-17. doi: 10.1016/j.actbio.2009.02.025. Epub Feb. 21, 2009.

Li et al., A single-use, scalable perfusion bioreactor system. BioProcess International. Jun. 2009;7(6):46-54 (even pages). Epub May 2009.

Lin et al., Biocompatibility of poly-DL-lactic acid (PDLLA) for lung tissue engineering. J Biomater Appl. Oct. 2006;21(2):109-18. Epub Jan. 27, 2006.

Nichols et al., Engineering of a complex organ: progress toward development of a tissue- engineered lung. Proc Am Thorac Soc. Aug. 15, 2008;5(6):723-30. doi: 10.1513/pats.200802- 022AW.

Rashid et al., Tissue engineering of a hybrid bypass graft for coronary and lower limb bypass surgery. FASEB J. Jun. 2008;22(6):2084-9. doi: 10.1096/fj.07-096586. Epub Jan. 18, 2008.

Reneker et al., N anometre diameter fibres of polymer, produced by electrospinning. Nanotechnol. Sep. 1996;7(3):216-23.

Sato et al., Replacement of the left main bronchus with a tissue-engineered prosthesis in a canine model. Ann Thorac Surg. Aug. 2008;86(2):422-8. doi: 10.1016/j.athoracsur.2008.04.015.

Teebken et al., Tissue engineering of vascular grafts: human cell seeding of decellularised porcine matrix. Eur J Vase Endovasc Surg. Apr. 2000;l9(4):381-6.

Vasita et al., Nanofibers and their applications in tissue engineering. Int J Nanomedicine. 2006; 1(1):15-30.

Niklason L E et al.; "Functional arteries grown in vitro"; Science, American Association for the Advancement of Sciene, US; vol. 284, No. 5413; Apr. 16, 1999; pp. 489-493, XP002200891; http://science.sciencemag.org/content/284/5413/489?ck=nck.

* cited by examiner

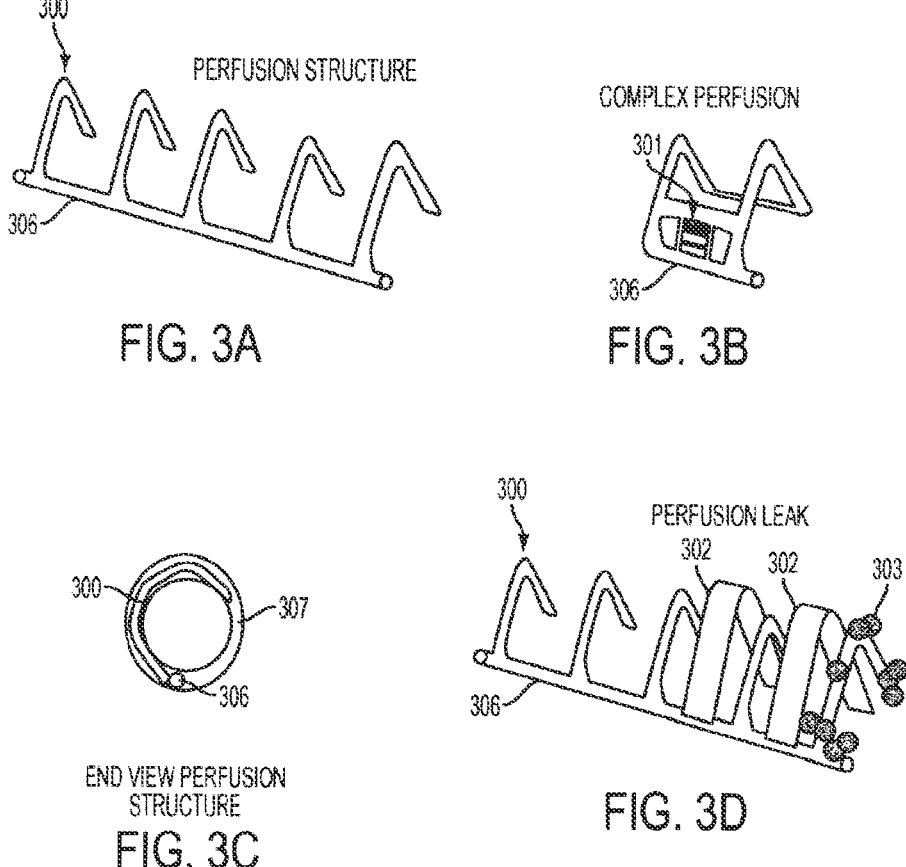
FIG. 3A
FIG. 3B
FIG. 3C
FIG. 3D
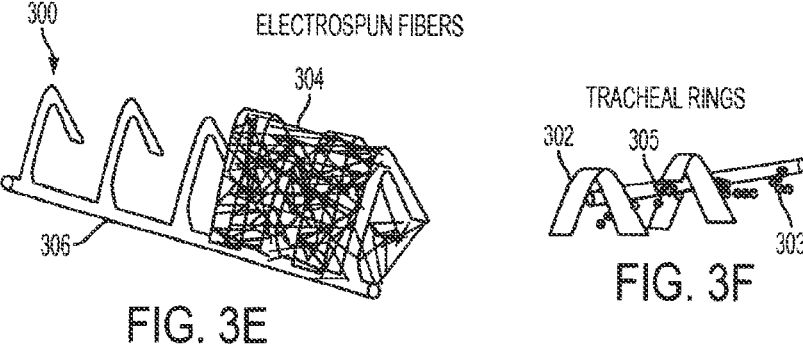
FIG. 3E
FIG. 3F

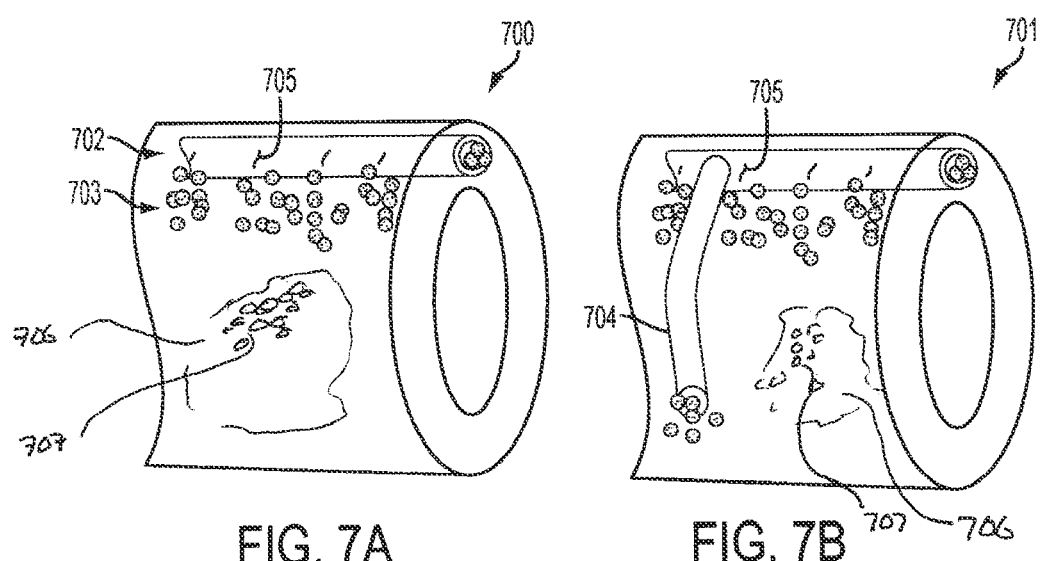
FIG. 7A                    FIG. 7B

SYNTHETIC SCAFFOLDS

CROSS-REFERENCE TO RELATED APPLICATION(S)

This Application is a divisional application of U.S. Non-provisional application Ser. No. 14/760,014 filed Jul. 9, 2015 now issued as U.S. Pat. No. 11,284,987 on Mar. 29, 2022. U.S. Nonprovisional application Ser. No. 14/760,014 is national stage filing under U.S.C. § 371 of International Application PCT/US2014/010941, entitled "SYNTHETIC SCAFFOLDS" with an international filing date of Jan. 9, 2014 which claims priority under 35 U.S.C. § 119(e) to U.S. Provisional Application Ser. No. 61/769,725, entitled "SYNTHETIC ORGANS" filed on Feb. 26, 2013, and to U.S. Provisional Application Ser. No. 61/750,788, entitled "SYNTHETIC ORGANS" filed on Jan. 9, 2013, which are herein incorporated by reference in their entireties.

BACKGROUND

Engineered tissues or organs can be produced ex vivo (for example in a bioreactor) and implanted into a host (e.g., a human patient) in order to replace or supplement an injured, diseased, or otherwise failing organ in the host. Engineered tissues or organs can be produced in a bioreactor by cellularizing a support structure referred to as a scaffold. Current techniques for producing scaffolds that can be cellularized ex vivo include methods that involve decellularizing a natural organ or tissue to produce an acellular scaffold of natural structural material, or methods that involve configuring a synthetic material to mimic a shape of a natural scaffold.

SUMMARY

Aspects of the invention relate to a combination of techniques and/or materials that can be used to form a synthetic scaffold for solid and/or hollow organs or tissue. In some embodiments, a scaffold may mimic a natural scaffold or several features of a natural scaffold. However, a synthetic scaffold can be different from a natural scaffold, because in order to achieve a satisfactory functional performance license may be taken to create structural and functional features that do not mimic all aspects of a biological scaffold. In some embodiments, a synthetic scaffold can include a combination of one or more structural components that mimic natural structures and one or more structural components that are different from natural structures. It should be appreciated that a synthetic scaffold described herein can include a combination of natural and synthetic material. In some embodiments, aspects of the invention relate to methods and compositions for preparing synthetic tissues or organs based on one or more different synthetic materials and/or a combination of different configurations of synthetic material(s).

In some embodiments, a scaffold for a synthetic organ is prepared using two or more different materials. In some embodiments, a first material is used to provide a first structural and/or functional property and a second material is used to provide a second structural and/or functional property. For example, a first material may be used to provide support for an engineered organ scaffold (e.g., structural support by providing for example a physical support network, and/or functional support network by providing for example one or more fluid conduits that allow gas or liquid materials to be introduced to one or more locations within the synthetic organ), and a second material may be used to provide a support for cellularization (e.g., by providing a biologically compatible network at a cellular scale, for example a porous layer of material that includes cellular scale pores). In some embodiments the first material and second material have different mechanical properties.

In some embodiments, a synthetic scaffold includes several (e.g., two or more, for example, 3, 4, 5, 6, 7, 8, 9, 10 or more) different structural and/or functional components manufactured from different materials and/or different manufacturing techniques. This allows different materials, and/or material(s) manufactured in different ways (e.g., printed, electrospun, molded, extruded, cast, lithographically produced, etc.) that are adapted for different aspects of organ structure and/or function to be combined to form a single synthetic organ scaffold.

In In some embodiments, a synthetic scaffold is designed to mimic the structures of a natural organ or tissue. In some embodiments, a synthetic scaffold is designed to be compatible with a transplantation site within a host body but does not mimic all of the structures or features of a natural organ or tissue. For example, a synthetic organ or tissues may be designed to fit within one or more physical parameters of a transplantation site of a host, in vivo or ex vivo. Physical parameters can include one or more of the size, shape, permeability, mechanical features (e.g., viscoelasticity) attachment site(s), vascularization configuration(s), neural configuration(s), or other parameters of a transplantation site in a host. However, a synthetic organ or tissue may provide only one or a subset of functions of a natural organ. In some embodiments, a synthetic organ or tissue provides one or more cell attachment sites that are connected to one or more perfusion pathways. In some embodiments, one or more perfusion pathways are connected to the vasculature of a subject (e.g., a human subject).

It should be appreciated that in some embodiments a scaffold may be provided without any cellular material. However, in some embodiments a scaffold may be cellularized with one or more different cell types. In some embodiments, a scaffold is cellularized with one or more of the following cells: adipocytes, adrenal cells, allogeneic cells, alveolar macrophages, ameloblasts, APUD cells, astrocytes, autologous cells, B cells, basophil granulocytes, boettcher cells, bone cells, bone marrow cells, cancer cells, cardiomiocytes, cartilage cells, cementoblasts, chondroblasts, chondrocytes, chromaffin cells, Clara cells, corticotropes, cytotoxic T cells, D cells, dendritic cells, dermal cells, ECL cells, endothelial cells, enterochromaffin cells, enteroendocrine cells, eosinophil granulocytes, epithelial cells, extraglomerular mesangial cells, fibroblast-like cells, fibroblasts, G cells, gastric cells, gastric chief cells, glial cells, glioblasts, goblet cells, gonadotropes, granulocytes, hair cells, hematopoietic stem cells, hepatocytes, hypersegmented neutrophils, I cells, immortalized cells, induced pluripotent stem cells, intraglomerular mesangial cells, islet cells, juxtaglomerular cells, K cells, keratinocytes, kidney cells, Kupffer cells, lactotrophs, Leydig cells, liver cells, lymphocytes, macrophages, macula *densa* cells, magnocellular neurosecretory cells, mast cells, megakaryocytes, melanocytes, mesenchymal stem cells, microglial cells, monocytes, monocytes, muscle cells, myeloid cells, myoblasts, myocardiocytes, myocytes, myotubes, natural killer T cells, neuronal cells, neutrophil granulocytes, nevus cells, odontoblasts, oligodendrocytes, oocytes, osteoblasts, osteoclast, osteocytes, osteogenic cells, oxyphil cells, paneth cells, parafollicular cells, parathyroid cells, parathyroid chief cells, parietal cells, pericytes, pineal cells, pinealocytes, pituitary cells, platelets, pneumocyte, podocytes, progenitor cells, regulatory T cells, reticular cells found in bone marrow stroma, reticulocytes, S cells, Sertoli cells, skin cells, smooth muscle cells, somatotrope, spermatozoa, stellate cells, stem cells, stromal cells, T cells, T helper cells, tendon cells, thrombocytes, thyroid cells, thyroid epithelial cells, thyrotropes, trichocytes, type I pneumocytes, type II pneumocytes, and umbilical cord cells.

In some embodiments, a scaffold is provided with one or more (e.g., 2, 3, 4, 5, or more) different structural and/or functional components that are useful for tissue or organ growth ex vivo (e.g., in a bioreactor). For example, some features of a scaffold may be designed to allow material (e.g., cells, nutrients, or other material) to be distributed in a manner that supports initial cellularization and/or subsequent cell growth and development in a bioreactor. For example, a scaffold may include or define one or more fluid conduits and/or patterns thereof that form a perfusion pathway that can be used to deliver material (e.g., cells, nutrients, growth factors, oxygen, etc.) and/or remove material (e.g., waste products, carbon dioxide, excess nutrients, toxins, etc.). In some embodiments, a scaffold is provided with one or more (e.g., 2, 3, 4, 5, or more) different structural and/or functional components that are useful to support and maintain an engineered tissue or organ during a transplantation procedure (for example during the transfer from a bioreactor to a host subject). In some embodiments, a scaffold is provided with one or more (e.g., 2, 3, 4, 5, or more) different structural and/or functional components that are useful to support growth, development, and/or viability of an engineered tissue or organ after it is transplanted into a host subject. It should be appreciated that structural and/or functional features that are useful for tissue or organ growth ex vivo also may be useful to support a tissue or organ during and/or after transplantation into a host. However, in some embodiments, different structural and/or functional features may be useful at different stages. For example, certain features that are useful to distribute cells or other material during growth and development in a bioreactor may not be useful after transplantation into a host.

In In some embodiments, a synthetic scaffold includes a combination of macro-scaffold and micro-scaffold components that are formed using different production techniques. In some embodiments, a synthetic scaffold includes an external macro-scaffold that provides structural support and/or protection for an internal space. The internal space can include one or more perfusion paths. In some embodiments, a network of internal perfusion pathways is provided. The network can include one or more branched trees of interconnected perfusion pathways. A perfusion pathway can include conduits of different sizes (e.g., different diameters). In some embodiments, two or more (e.g., 2, 3, 4, 5, or more) separate perfusion pathways that are not in fluid connection with each other (e.g., within the scaffold) are provided in the internal space. It should be appreciated that each perfusion pathway may include one or more connections to the external space to allow for fluid exchange (e.g., influx and/or efflux) with the internal space. In addition to one or more perfusion pathways, an internal space may include additional structural elements. For example, a porous material may be provided to support cell growth. In some embodiments, porous support material can be disposed around a perfusion pathway. In some embodiments, porous support material can be provided at one end of a perfusion pathway (e.g., at the smaller ends of a branched perfusion pathway). In some embodiments, other structural elements may be included to provide a substrate or other form of structural support for the porous material. In some embodiments, the porous material includes natural material (e.g., collagen or natural fibrous material). In some embodiments, the porous material includes an electrospun fibrous material (e.g., one or more electrospun nanofibers). The porous material may be in the form of a sheet or bundle or other three-dimensional configuration.

In some embodiments, one or more first structural elements (e.g., perfusion pathways) of a hybrid scaffold are provided to promote cellularization and/or development (e.g., growth and/or differentiation) of different cell types to form a synthetic organ or tissue. In some embodiments, one or more second structural elements (e.g., perfusion pathways) of a hybrid scaffold are provided to support cell viability after growth and differentiation of the synthetic organ or tissue. In some embodiments, first and second structural elements are the same (e.g., the same structural elements can be useful to promote appropriate cell growth and differentiation and subsequent cell viability). In some embodiments, first and second structural elements are different. For example, a first element is used to support and promote appropriate cell growth and differentiation during organ or tissue formation, but is not used subsequently. In some embodiments, one or more first elements are degradable (e.g., biodegradable). However, one or more first elements may persist after growth and differentiation even if they are not used to support the subsequent viability and function of the synthetic organ or tissue. These embodiments can allow for organ expansion from design or materials selected so the growth of the scaffold is simulated by a scaffold increase in size and then the cellularization takes place on the expanded scaffold. In some embodiments, one or more scaffold components can simulate organ growth by expanding over time. In some embodiments, a perfusion pathway is designed to include one or more regions that can expand. In some embodiments, wall material can be sufficiently flexible or elastic to accommodate growth and/or expansion of a synthetic tissue or organ (along with the underlying scaffold), i.e. can simulate growth by expanding to a cue. In some embodiments, the pattern of a perfusion network is designed to accommodate tissue or organ growth or expansion through rearrangement (e.g., straightening) of one or more pathway conduits. In some embodiments, a synthetic tissue or organ can grow or expand in response to a cue. In some embodiments, a cue can be one or more growth factors (e.g., that can be delivered by a perfusion pathway described herein). Accordingly, two or more different components of a scaffold can be designed to expand or rearrange in response to synthetic tissue or organ growth (e.g., associated with cell growth and proliferation), i.e. the structure can simulate growth by expanding to a cue or response to cellular or tissue growth. Accordingly, scaffolds can incorporate either materials that expand or structural features that allow for growth of the scaffold.

In some embodiments, two or more different perfusion pathways can be used to deliver two or more different materials (e.g., one or more each of different cells types, growth factors, nutrients, gases, etc.) to different or overlapping regions of a scaffold. In some embodiments, different materials are delivered to different regions at different times as a synthetic organ or tissue grows or expands.

In In some embodiments, aspects of the invention relate to methods, compositions, and articles for producing artificial (e.g., synthetic) tissues, organs, or portions thereof that can be implanted into a host (e.g., a human host) to replace diseased or injured tissues, organs, or portions thereof. In some embodiments, aspects of the invention relate to scaffolds that are used for tissue growth. Scaffolds generated as described herein can be seeded with appropriate cell types to produce artificial tissues or organs or portions thereof for transplantation into a host. These and other aspects are described in more detail herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 3A-3F depict non-limiting examples of organ perfusion channels;

FIG. 7A-7B depict a non-limiting example of a synthetic delivery system that can be used to deliver material to predefined positions on or in a synthetic organ or tissue.

DETAILED DESCRIPTION

Figure 1A:
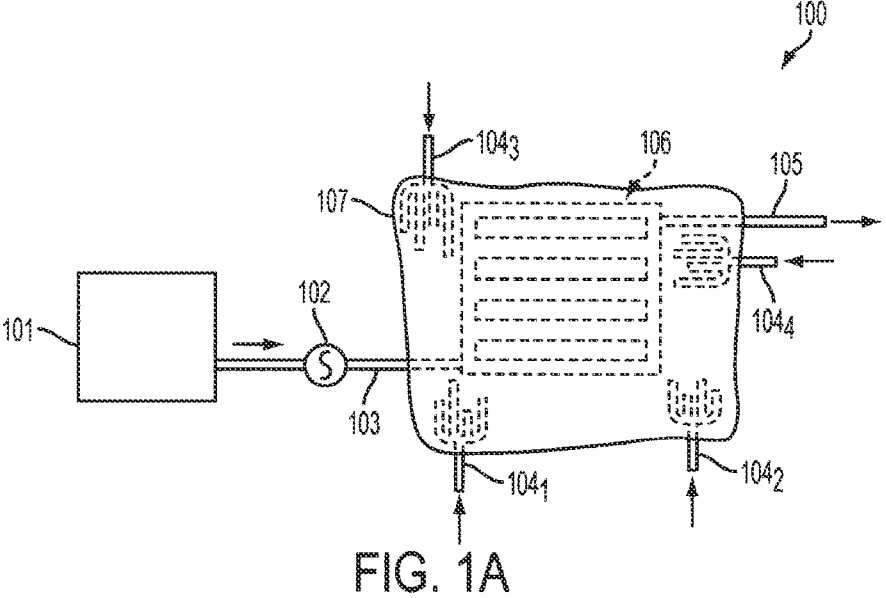
FIG. 1A depicts a non-limiting example of an organ scaffold (physical support) having multiple perfusion networks.

In some aspects, the disclosure provides methods, compositions, and devices for producing scaffolds that can support synthetic organs or tissue in a bioreactor, and/or during or after transplantation into a host subject (e.g., a human patient). In some embodiments, aspects of the disclosure relate to synthetic scaffolds that include two or more different types or configurations of material that provide different structural and/or support functions for an engineered organ or tissue. It should be appreciated that in some embodiments certain scaffold features that are useful during cellularization and development in a bioreactor are not required subsequently when an engineered tissue or organ is implanted into a host subject. Accordingly, a synthetic scaffold may include structural or functional features that are not found in natural organ or tissue scaffolds. In some embodiments, a synthetic scaffold is designed to include one or more perfusion pathways. Perfusion pathways may be used to deliver material to a synthetic scaffold to support tissue growth, development, and/or viability.

In some embodiments, a combination of two or more materials and/or manufacturing techniques are used to produce a synthetic organ scaffold In some embodiments, a natural material may be combined with a synthetic material. A synthetic material may be electrospun, printed, molded, cast, or produced using any suitable synthetic technique. In some embodiments, a combination of electrospun, printed, molded, cast and/or other synthetic material may be used, and optionally may be combined with one or more natural materials. In some embodiments, a synthetic material may have a surface that is modified or coated (e.g., with another material) to promote cellularization and/or cell growth and viability. It should be appreciated that different techniques and/or materials may be better suited for different components of a synthetic scaffold. In some embodiments, larger scale components (e.g., macro-scale scaffold components may be printed, molded). In some embodiments, smaller scale components (e.g., micro-scale or nano-scale scaffold components) may be electrospun. However, it should be appreciated that any technique may be used for different sized structures depending on the desired structural and functional properties of a scaffold, and the resolution and materials used by certain techniques. In some embodiments, an organ or tissue scaffold may be designed to support a synthetic organ or tissue that is for use in vivo (for example in a host subject). However, in some embodiments, an organ or tissue scaffold may be designed to support a synthetic organ or tissue for use ex vivo (for example to provide one or more functions ex vivo). It should be appreciated that scaffolds may be designed to support cells for different lengths of time. In some embodiments, a scaffold may be designed to support cells for an extended period of time (several months, a year, or more). However, in some embodiments, a scaffold may be designed to support cells for a short term (e.g., less than one month). Scaffolds designed for longer term use may include one or more structural and functional support elements that help provide a suitable environment for long-term cell growth and survival. For example, scaffolds may include networks of channels and/or other structures that allow for nutrients to be supplied to cells and for waste material to be removed from cells on the scaffold.

In some embodiments, functional devices or components thereof are produced using biologically compatible parts that include biologically compatible scaffolds and/or scaffolds coated with one or more cell types In some embodiments, different layers or components of a synthetic scaffold are produced using different materials and/or techniques (e.g., different layers of a tracheal scaffold that correspond to muscle layers, cartilage layers or structures, and/or connective tissue layers).

In some embodiments, perfusion pathways (e.g., channels or networks) are provided to a synthetic scaffold. In some embodiments, a perfusion pathway is used during the growth and development of cells or tissue on the synthetic scaffold. In some embodiments, a perfusion pathway is used to maintain cell viability after a tissue or organ is formed on a synthetic scaffold (e.g., during and/or after transplantation into a host subject). In some embodiments, a perfusion pathway has a geometry that is similar to a natural vascular network. However, a perfusion pathway can have a geometry that is different from a natural vascular network as aspects of the invention are not limited in this respect.

Different perfusion pathways having different configurations and properties can be used to control the distribution pattern and timing of different materials to a scaffold as described in more detail herein. As used herein the term "perfusion pathway" refers to a set of one or more confined or partially confined passages configured and arranged to guide flow of a fluid within and/or on a material (e.g., an organ scaffold). In some embodiments, a perfusion pathway is in fluid communication (e.g., fluidically connected) with one or more inlets through which a fluid is supplied to the perfusion pathway. In some embodiments, a perfusion pathway is in fluid communication (e.g., fluidically connected) with one or more outlets through which a fluid exits the perfusion pathway. In some embodiments, a perfusion pathway comprises one or more fluid flow surfaces that are permeable, partially permeable or differentially permeable with respect to one or more components suspended, dispersed, dissolved or otherwise present in the fluid. Thus, in some embodiments, one or more components of a fluid flowing or contained within a passage of a perfusion pathway can diffuse or permeate into a material surrounding the passage through a fluid flow surface. It should be appreciated that the terms passage, conduit, and channel are used interchangeably herein unless indicated by context or otherwise. In some embodiments, a conduit or channel of a pathway is a tubular conduit or tubular member. It should be appreciated that channels or conduits of a pathway can be enclosed by a wall such as a cylindrical wall to define an inner volume that is separated from the surrounding scaffold by the wall. A pathway wall can be manufactured from one or more different materials described herein and has an inner surface and an outer surface (that can be modified and/or coated differently in some embodiments). In some embodiments, a perfusion pathway comprises at least one passage having a cross-sectional dimension (e.g., length, width, height, diameter) in a range of 0.1 μm to 1 mm, 0.1 μm to 10 mm, 0.1 μm to 25 mm, 0.1 μm to 100 mm, 1 μm to 1 mm, 1 μm to 10 mm, 1 μm to 25 mm, 1 μm to 100 mm, 10 μm to 1 mm, 10 μm to 10 mm, 10 μm to 25 mm, 10 μm to 100 mm, 100 μm to 1 mm, 100 μm to 10 mm, 100 μm to 25 mm, or 100 μm to 100 mm. In some embodiments, a perfusion pathway comprises 1 to 10, 1 to 50, 1 to 100, 1 to 250, 10 to 50, 10 to 100, 10 to 250, 50 to 100, 50 to 250, 100 to 250, or 100 to 1000 confined or partially confined passages configured and arranged to guide flow of a perfusion fluid within and/or on a material (e.g., an organ scaffold) from at least one inlet to at least one outlet. In some embodiments, a perfusion pathway comprises a branched network of passages. In some embodiments, a perfusion pathway comprises an unbranched network of passages. In some embodiments, a perfusion pathway comprises a network of randomly orientated fluid passages. In some embodiments a perfusion pathway comprises a network of non-randomly orientated fluid passages. In some embodiments, a perfusion pathway does not comprise randomly orientated passages. In some embodiments, a perfusion pathway comprises isotropically orientated passages. In some embodiments, a perfusion pathway comprises anistropically orientated passages. In some embodiments, a perfusion pathway is a set of defined passages, and not merely a void space between physical elements of a material. In some embodiments, one or more physical properties of the walls (e.g., porosity, permeability, presence of orifices or other openings of any shape along the sides or at the ends, etc.) of a perfusion pathway allow material to be delivered or removed in a particular pattern that is define by the relative porosity and or permeability patterns of the pathway walls.

A perfusion pathway can be used to deliver material (e.g., cells, growth factors, nutrients, etc.) to one or more defined regions within a 2- or 3-dimensional synthetic scaffold. In some embodiments, perfusion pathways are provided to remove material (e.g., waste or toxins) from one or more defined regions within a 2- or 3-dimensional synthetic scaffold. In some embodiments, a perfusion pathway includes one or more inlets and/or outlets. In some embodiments, one or more inlets are designed to be connected to a fluid delivery device (e.g., a syringe or a pump). In some embodiments, one or more outlets are designed to be connected to a waste collection, pump, or other fluid handling device. However, in some embodiments, outlets can include valves or similar devices useful to prevent a pressure buildup in the pathway during fluid delivery.

In some embodiments, one or more materials described herein may be used to coat (e.g., cover or partially cover) a surface (e.g., outer surface) of a perfusion pathway or portion thereof or of a scaffold or component thereof that is designed to be used in a cellular environment (e.g., in vivo or ex vivo).

In some embodiments, one or more materials described herein may be used to coat (e.g., cover or partially cover) a surface (e.g., outer surface) of a manufactured device or component thereof that is designed to be used in a cellular environment (e.g., in vivo or ex vivo). For example, one or more materials may be used to coat a surface of a perfusion pathway or scaffold or other device that is implanted in subject. A device can be a surgical screw, a stent, an artificial joint, an artificial valve (e.g., a heart valve, for example an left ventricular assist device (LVAD), for example having a metal surface coated with a material or scaffold that is cellularized with autologous or allogeneic cells to reduce the damage that synthetic materials may have on cells) or other implantable device or component thereof. In some embodiments, a coating material is used to provide a suitable matrix for cellularization (e.g., with autologous or allogenic cells). This can be useful to enhance the biocompatibility of one or more perfusion pathways, other scaffold components, devices, or components thereof (e.g., prior to implantation in a host). In some embodiments, a perfusion pathway, scaffold, device, or a portion thereof is coated with an electrospun fiber to provide a suitable substrate for cellularization.

In some embodiments, the outer surface of a perfusion pathway or a portion thereof (or a portion of a scaffold that incorporates one or more perfusion pathways) is designed to have a porous surface having pores ranging from around 10 μm to about 100 micron in diameter that can promote cellularization. However, it should be appreciated that pores of other sizes also can be included. In some embodiments, a surface layer of a perfusion pathway or other scaffold component is synthesized using fibers that include one or more dissolvable particles that can be dissolved during or after synthesis (e.g., by exposure to a solvent, an aqueous solution, for example, water or a buffer) to leave behind pores the size of the dissolvable particles. In some embodiments, the particles are included in the polymer mix that is pumped to the nozzle of an electrospinning device. As a result, the particles are deposited along with the fibers. In some embodiments, the electrospinning procedure is configured to deposit thick fibers (e.g., having an average diameter of several microns, about 10 microns, and thicker). In some embodiments, if the fibers are deposited in a dense pattern, one or more fibers will merge prior to curing to form larger macro structures (e.g., 10-100 microns thick or more). In some embodiments, these macrostructures can entangle two or more layers of fibers and or portions (e.g., fibers) from two or more different components of a surface of a perfusion pathway or other scaffold component thereby increasing their mechanical integrity. In some embodiments, when such macrostructures are formed (e.g., via electrospinning as described herein) at one or more stages during synthesis (e.g., to connect two or more layers and/or components), the surface of the macrostructure(s) can be treated (e.g., etched or made porous using dissolvable particles as described herein) in order to provide a surface suitable for cellularization.

These and other features can be used to promote the integrity and/or biocompatibility of one or more perfusion pathway components along with other scaffold components that are used to support the growth and development (e.g., in a bioreactor) of a synthetic tissue or organ prior to, during, and/or after transplantation into a host subject (e.g., a human patient).

Non-limiting examples of perfusion pathway systems that can be incorporated into a tissue or organ scaffold are illustrated by reference to FIG. 1. FIG. 1A depicts a non-limiting example of system 100 comprising an organ scaffold (physical support) 107 having multiple perfusion networks. System 100 is configured with a reservoir 101 housing a fluid (e.g., a nutrient medium). Reservoir 101 is fluidically connect with the organ scaffold 107 through inlet 103. System 100 include at least one fluid transfer device 102 (e.g., a pump) configured and arranged to transfer fluid from the reservoir 101 to organ scaffold 107.

Organ scaffold 107 is configured with a first perfusion network 106 that includes both an inlet 103 and an outlet 105. The inlet 103 and outlet 105 are configured and arranged such that fluid can be circulated through the first perfusion network 106. The first perfusion network 106 may be configured and arranged to have a network of fluid channels passing through the organ scaffold 107 that permit fluid to be transferred through the organ scaffold 107 (e.g., to supply nutrients or other materials, control temperature or pH conditions, etc.). The first perfusion network 106 may be configured and arranged to have a network of fluid channels, in which the channels are of two or more different sizes or shapes. The channels may comprise straight or curvilinear sections within the organ scaffold 107.

System 100 also includes at least one second perfusion network 104$_{1-4}$ having inlets that provide a fluid to the organ scaffold 107. For example, one or more second perfusion network 104$_{1-4}$ could comprise a network of branched structures within the organ scaffold 107 that have ends as opposed to reconnecting to an outlet. In some examples, this second perfusion network 104$_{1-4}$ could be used to deliver material to target regions of a synthetic organ (for example by having open ends, or porous ends or porous sides, etc.) grown on the organ scaffold 107. In some embodiments, the at least one second perfusion network 104$_{1-4}$ is configured and arranged to result in a net flow into a synthetic organ grown on the organ scaffold 107. In some embodiments, this net flow could either be accommodated by i) a slow flow that is coordinated with a growth rate or ii) material (e.g., fluid) being lost into the medium that is bathing the synthetic organ (as opposed to being withdrawn through the outlet and recirculated, for example). Inlets of the at least one second perfusion network 104$_{1-4}$ can be fluidically connected one or more reservoirs or other fluid sources. However, it should be appreciated that in some embodiments a network such as one of 104$_{1-4}$ can act as an outlet and be fluidically connected to one or more pumps or reservoirs that removes fluid (and, for example, material such as waste material) from within one or more regions of a scaffold.

Figure 1B:
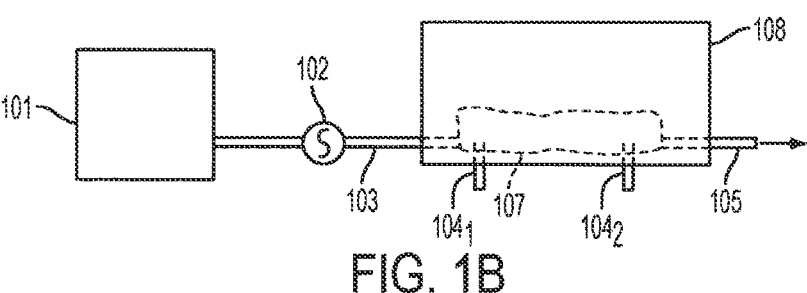
FIG. 1 B depicts a non-limiting example of an organ scaffold in a bioreactor (a container)

FIG. 1B depicts a non-limiting example of an organ scaffold 107 in a bioreactor 108 (a container). It should be appreciated that the bioreactor 108 may be connected to one or more pumps, controllers, reservoirs, monitors, etc. to control and monitor growth of the organ. For example, flow of a perfusion media into or through the organ scaffold may be monitored, e.g., using infrared spectroscopy.

In some embodiments, fluid flow within a pathway can be monitored by a device such as an infrared device that can detect changes in temperature or other physical properties associated with fluid flow. In some embodiments, a bioreactor may include one or more infrared detectors that can be used to monitor the extent of fluid flow within a scaffold (for example to determine whether appropriate temporal and spatial distributions of one or more materials of interest are being delivered).

It should be appreciated that in some embodiments, a synthetic tissue or organ scaffold can be sufficiently porous and/or permeable prior to cellularization to allow oxygen, nutrients, and other material to readily circulate throughout the volume of the scaffold (for example if the scaffold is bathed with a cellular or nutrient medium within a bioreactor). However, as the scaffold is progressively cellularized and as the cells grow and replicate on the scaffold, the overall porosity and permeability properties of the scaffold can decrease and it can be useful to have one or more conduits or networks of conduits on or within the scaffold to help deliver fluids containing oxygen, nutrients, additional cells, etc., and/or to remove waste products, toxins, or other unwanted material from within the scaffold. These processes can help promote healthy and sustainable growth and development of cells within a tissue or organ scaffold (e.g., within a bioreactor).

Accordingly, it should be appreciated that in some embodiments one or more perfusion pathways can be used differently at different stages of a synthetic organ or tissue growth or differentiation. In some embodiments, different materials can be delivered to different regions of a scaffold at different times. In some embodiments, a first fluid comprising cells is delivered via a first pathway (e.g., a perfusion pathway that is on and/or within a scaffold and that is connected to a fluid delivery device in a bioreactor) to cellularize one or more portions of a scaffold during a cellularization phase. In some embodiments, a second fluid comprising one or more growth factors is delivered to a cellularized scaffold via a second pathway (e.g., a perfusion pathway that is on and/or within a scaffold and that is connected to a fluid delivery device in a bioreactor). The first and second pathways may be the same or different in different embodiments. In some embodiments, a third fluid comprising one or more nutrients and/or oxygen is delivered to a cellularized scaffold via a third pathway (e.g., a perfusion pathway that is on and/or within a scaffold and that is connected to a fluid delivery device in a bioreactor). In some embodiments, the third pathway is the same as the same as the second pathway. In some embodiments, the third pathway is the same as the first pathway. However, in some embodiments the third pathway is different from the second and/or the first pathway. It should be appreciated that growth factors and/or nutrients also may be present in the first fluid. It also should be appreciated that the second and third fluids can be cell-free but may include both growth factors and nutrients and/or oxygen.

In some embodiments, pathways that are used during cellularization and/or growth of a synthetic organ or tissue are not used during and/or after transplantation into a subject. For example, such pathways may be connected to pumps or other fluid delivery devices in the context of a bioreactor, but disconnected and not used again after transplantation into a subject. In some embodiments, one or more such pathways may have biodegradable or resorbable walls that do not persist intact for a sustained period after transplantation. However, it should be appreciated that in some embodiments the walls are manufactured of durable material even if the pathways are not used after transplantation as aspects of the disclosure are not limited in this respect. In some embodiments, if a durable material is used to synthesize the pathway walls, the outer surface can be modified and/or coated (e.g., with a biocompatible micro or nano fiber material) to promote cellularization and/or to avoid inflammatory or immune responses.

In some embodiments, one or more perfusion pathways can be used to transport oxygen (and/or other material) into a synthetic tissue or organ during surgery (e.g., after removal from a bioreactor but before implantation into a host subject). Accordingly, in some embodiments a synthetic perfusion pathway can be incorporated into a scaffold so that it can act as a shunt (e.g., for delivering oxygen in a fluid or as a gas, for example a humidified gas) during surgery. This pathway can include an inlet and an outlet that can be connected to a supply of oxygen and/or other fluid. In some embodiments, an oxygen shunt is connected to an appropriate oxygen supply during surgery. In some embodiments, this pathway is not connected to other fluid pathways in the scaffold, some of which may be vascular pathways that are sutured to the subject's vasculature during surgery. However, by using a shunt (e.g., a separate pathway for delivering oxygen and/or other nutrients) surgery can proceed without needing to connect the vasculature to the engineered tissue or organ for it to survive during surgery. After surgery, once the synthetic tissue or organ is appropriately vascularized, the shunt can be disconnected. In some embodiments, a shunt as described herein may be maintained for several days after surgery to allow the synthetic organ or tissue to survive during the period that vascular connections to the transplanted tissue or organ are established and/or strengthened within the host subject.

In some embodiments, a perfusion pathway has different properties at different points along the pathway. For example, the wall of a perfusion pathway can be less permeable at the inlet than at a location along the pathway where material (e.g., cells, growth factors, fluid, etc.) is being targeted. For example, the wall of a perfusion pathway may be permeable, semi-permeable, and/or porous, in certain regions of the pathway. The degree of permeability and/or porosity may be different in different regions of the pathway. In some embodiment, the wall(s) of a perfusion pathway are permeable to gases (e.g., $O_2$, $CO_2$) nutrients, cellular waste products, buffers, salts, polysaccharides, growth factors, cytokines, signaling molecules, large proteins or other macromolecules. In some embodiment, the wall(s) of a perfusion pathway are permeable to cells. In some embodiment, the wall(s) of a perfusion pathway are permeable to molecules having a molecular weight of up to 0.1 kDa, up to 1 kDa, up to 10 kDa, up to 50 kDa, up to 100 kDa, up to 500 kDa, up to 1000 kDa, or up to 5000 kDa. In some embodiments, the wall of a perfusion pathway is permeable to molecules in a range of 0.1 kDa to 10 kDa, 0.1 kDa to 50 kDa, 0.1 kDa to 100 kDa, 1 kDa to 10 kDa, 1 kDa to 50 kDa, 1 kDa to 100 kDa, 1 kDa to 1000 kDa, 10 kDa to 50 kDa, 10 kDa to 100 kDa, 10 kDa to 1000 kDa, 100 kDa to 1000 kDa, 500 kDa to 1000 kDa or 500 kDa to 5000 kDa.

In some embodiments, a perfusion pathway may be produced using a material that is different from the material of other structural element of a synthetic scaffold.

For example, a perfusion pathway may be electrospun and then attached to a molded or cast support that provides an organ or tissue shape or structure.

In some embodiments, a perfusion pathway provides at least 20% (e.g., at least 25%, at least 40%, at least 50%, at least 60%, at least 75%, at least 80%, or more) of the perfusion and/or filtering function of a natural organ Accordingly, it should be appreciated that different manufacturing techniques may be used to produce different components of a synthetic scaffold. For example, a combination of manufacturing techniques can be used to create an exterior scaffold support membrane, a structural scaffold to provide physical durability, and other techniques for fibrous layers where cells may be seeded during or after production. In some embodiments, a synthetic organ scaffold can be manufactured from different components that are assembled. In some embodiments, an organ scaffold can be provided in the form of open parts that are attached to form a closed and complete structure. In some embodiments, different components or materials may be added to a synthetic scaffold sequentially. Accordingly, a perfusion pathway can be a separate insert or included into a structural element or both. In some embodiments, a perfusion pathway can comprise structural elements around which is synthesized or deposited a synthetic scaffold, in which the structural elements of the pathway remain intact. In some embodiments, a perfusion pathway can be formed by using temporary structural elements around which is synthesized or deposited a synthetic scaffold, in which the temporary structural elements are degraded or removed following synthesis or depositing of the synthetic scaffold, leaving a cavity within the synthetic scaffold that provides a perfusion pathway It should be appreciated that cells can be seeded during production of a synthetic scaffold, after production, and/or after implantation into a subject.

Different components of a synthetic scaffold can be attached using appropriate techniques. For example, molded or printed structures can be attached using physical suturing, clamps, other physical attachments, adhesives, heat, pressure, or a combination thereof. In some embodiments, molded or printed structures can be attached via welding, for example by heating, or using ultrasonic or laser techniques, and/or by chemical melting, or a combination thereof. In some embodiments, welds or other regions of material attachments or fusion can be introduced at one or more positions within a structure (or around a structure) to provide support (e.g., for suturing, etc.).

In some embodiments, a device includes a first outer support that can provide a framework or receptacle within which a second inner material can be disposed to support cell growth. The outer support can be a molded support in some embodiments. However, it can be produced using any suitable technique as aspects of the disclosure are not limited in this respect. In some embodiments, the second material includes electrospun fibers (e.g., micro or nano fibers). In some embodiments, a perfusion pathway is incorporated into the inner material. In some embodiments, the perfusion pathway is formed by the second material itself and is defined by the shape and configuration of the second material that is produced to form one or more conduits or branched networks of conduits within its volume. Accordingly, in some embodiments a pattern of conduits and branched networks of conduits can be defined by the three-dimensional pattern of material density within the volume of the second material. However, in some embodiments one or more conduits or branched networks of conduits are defined by a different material (e.g., in the form of one or more tubes that are interconnected or branched) that is placed within the second material. In some embodiments, the conduit material can be printed, molded, extruded, etc., or any combination thereof. In some embodiments, the conduit material can be embedded within the second material during synthesis. For example, if the second material is an electrospun fiber, it can be deposited on and around a network of conduits to form a perfusion pathway that is embedded within the second material.

In some embodiments, a perfusion pathway that is embedded within scaffold material (e.g., an electrospun material)

can include an inlet and/or an outlet that can be connected to a fluid system (e.g., including one or more pumps, syringes, or other devices for promoting the flow of fluid through the system).

In some embodiments, a perfusion pathway delivers material (e.g., nutrients, oxygen, etc.) along most or all (e.g., about 50-60%, 60-70%, 70-80%, 80-90%, 95%, or more) of its length within a scaffold. In some embodiments, a perfusion pathway is designed to include a plurality of parallel and/or branched conduits that delivery material to the scaffold. In some embodiments, most or all of the scaffold volume (e.g., about 50-60%, 60-70%, 70-80%, 80-90%, 95%, or more) is sufficiently near a perfusion pathway to receive sufficient oxygen, nutrients, or other material that is useful for cell growth, development, and or survival. In some embodiments, most of the scaffold volume is within 10 mm or less (e.g., 5-10 mm, about 5 mm, less than 5 mm, 1-5 mm, about 3 mm) of a portion of the perfusion pathway that is delivering material to the scaffold. Accordingly, in some embodiments, no electrospun fibers of the scaffold will be more than 10 mm (e.g., more than 1-5 mm, about 3 mm, or 510 mm) from a portion of a perfusion pathway that delivers material to the scaffold.

Accordingly, different organ scaffolds may be produced differently depending on their structural and/or functional requirements. For example, different organs or tissues may have different thicknesses, different structural elements (e.g., support rings or ribs, etc.), different porosity requirements, different perfusion requirements, different flexibility or elasticity requirements, etc., and these can be supported by different synthetic materials.

In some embodiments, aspects of the invention relate to methods for enhancing the integrity of synthetic organ constructs or natural organ constructs produced with different materials, including electrospun nanofibers, as structural and/or tissue scaffolds components.

In current uses of electrospun materials for scaffolds, problems arise when a second layer of electrospun material is placed on top of first layer that has already been spun. One problem is that the second layer is separate and not physically attached so it can delaminate from the first layer, making the scaffold potentially unstable. Accordingly, aspects of the disclosure relate to techniques that can be used to promote or maintain the structural integrity of scaffolds that include at least two different materials and/or configurations of material (for example for scaffolds that include one or more perfusion pathways that are associated with one or more structural supports).

Problems arising from the presence of separate (not physically attached) fibers also can occur for structures that are produced using a technique that involves stopping the electrospinning (e.g., to place an additional material into the structure of the scaffold and/or to combine a perfusion pathway into a scaffold structure for example) and then restarting the electrospinning (for example to spin over the additional material). Again, an unstable condition can exist with the two different electrospun layers being separate and not connected, resulting in potential separation, or delamination, of the two layers. This separation can release the additional material (e.g., a trapped solid entity that was intended to be part of the electrospun structure) and jeopardize the integrity of the entire construct.

Different approaches for enhancing the structural integrity of electrospun structures are described herein. It should be appreciated that each of these techniques can be used alone to reduce the risk of structural failure. However, in some embodiments, one or more of these techniques may be combined as aspects of the invention are not limited in this respect.

In some embodiments, a continuous structural element and/or one or more perfusion pathways are inserted within an electrospun nanofiber material. In some embodiments, the continuous element and/or perfusion pathway(s) can be incorporated (e.g., captured by electrospinning) into two or more layers or regions (e.g., formed by electrospun fibers that are not connected). It should be appreciated that the continuous element and/or perfusion pathway(s) can have any suitable shape (e.g., a coiled or approximately coiled shape). A continuous structural element can be generally elongate (e.g., long and thin, for example in the form of a string, fiber, tape or similar structure) and shaped to match the general 2- or 3-dimensional shape or contours of the synthetic material it is intended to support. However, the structural element can have other shapes including portions that are in the forms of discs or sheets or other more complex shapes. A structural element can be made of any suitable material, including, but not limited to, a metal, a plastic, a natural material, a fiber (e.g., an electrospun fiber), any suitable polymer, or any other material. One or more perfusion pathways(s) can have any configuration that is suited to their intended function. It should be appreciated that the geometry of a perfusion pathway (including for example the relative length and diameters of different regions of the pathway and/or the branching pattern and/or density of the pathway) and/or the distribution of orifices and/or regions of different relative permeabilities and/or porosities along different portions of the pathway can be designed to accomplish the input and/or output requirements of the pathway. For example, a pathway that is designed to delivery cells will have one or more orifices or other openings at certain positions that are sufficiently large to allow cells to be deposited at those positions within the scaffold.

In some embodiments, a perfusion pathway can follow the pattern of one or more support structures of a scaffold. In some embodiments, support structure(s) of a scaffold are portions of the scaffold that provide physical support to all or a portion of the scaffold. In some embodiments, support structure(s) of a scaffold are portions of the scaffold that provided physical support to a bulk of the scaffold. In some embodiments, a support structure comprises one or more structural elements that have a greater resistance to bending, compression and/or tension compared with a material (e.g., electrospun nanofiber material) deposited or present thereon. For example, support structures can include a plurality of ribs. Or, in some embodiments, a support structure can be continuous framework or skeleton that supports at least a portion of a scaffold. In some embodiments, a perfusion pathway can be attached to a support structure. In some embodiments, a perfusion pathway can be incorporated into a support structure (e.g., the support structure includes a hollow conduit that provides a perfusion pathway). In some embodiments, a perfusion pathway is not directly attached to a support structure, but can follow the shape and configuration of the support structure and be associated with the support structure via the surrounding scaffold material. In some embodiments, the continuous support structure provides a backbone that can be shaped to support a tubular structure. The backbone can be incorporated into a nanofiber structure to create a tubular structure that can have the shape of a trachea and be used as a basis for a tracheal implant. However, it should be appreciated that aspects of the disclosure can be used with other support structures for other organ or tissue scaffolds as aspects of the disclosure are not limited in this respect. Accordingly, a continuous support structure can be in any appropriate shape and can form the backbone of an electrospun structure for other organs.

In some embodiments, the continuous support structure (e.g., coiled backbone) can be electrically conductive or non-electrically conductive. In some embodiments, the continuous support structure (e.g., coiled backbone) can be a metallic or polymeric structure. In some embodiments, the continuous support structure (e.g., coiled backbone) can be made up of multiple materials. In some embodiments, the continuous support structure (e.g., coiled backbone) can be coated or non-coated.

In some embodiments, an electrically conductive support structure (e.g., coiled backbone) is an integral part of an electrospun nanofiber tubular synthetic organ structure. In some embodiments, the continuous support structure (e.g., coiled backbone) is selectively electrically charged. In some embodiments, the charge is positive, negative, alternating, biphasic, pulsed, ramped, etc. In some embodiments, the charge is selectively controlled and/or maintained in order to alter the bonding properties of electrospun nanofiber layers which come into contact with the backbone. In some embodiments, the purpose of this selective control is to reduce the likelihood (through above bonding) of delamination of electrospun nanofiber layers deposited on an organ structure (e.g., a tubular synthetic organ structure).

In some embodiments, the continuous support structure (e.g., coiled backbone) is an electrically conductive backbone that serves as the electrospinning mandrel for the purpose of creating an electrospun nanofiber tubular synthetic organ structure. In some embodiments, the electrical characteristics of the backbone are tuned to control the deposition of electrospun nanofibers anywhere along the entire dimension of the tubular synthetic organ structure. In some embodiments, the electrical characteristics of the backbone are tuned to provide deposition of electrospun nanofibers which is uniform, differential, alternating, mixed, aligned, non-aligned etc. In some embodiments, the deposition is utilized to create an electrospun nanofiber tubular synthetic organ structure with specific mechanical or biological properties including: tensile strength, rotation, compression, range of motion, bending, resistance, compliance, degrees of freedom, gas permeability, pore size, cellular engraftment, differentiation, proliferation, infiltration, angiogenesis, vascularization, etc., or any combination thereof. In some embodiments, a support structure is designed and synthesized to incorporate one or more channels that can be used as perfusion pathways (e.g., to promote growth, development, and/or viability or engineered tissue). However, in some embodiments one or more perfusion channels are synthesized independently and subsequently attached to or otherwise associated with the support structure In some embodiments, aspects of the invention relate to an electrospun nanofiber tubular synthetic organ structure wherein the continuous support structure (e.g., the coiled backbone) and/or perfusion pathway possesses integrated micro and/or nano features which combine with complimentary counterpart micro and/or nano features of the electrospun nanofiber layers which it contacts, thereby enhancing the bonding properties between the continuous support structure and/or perfusion pathway and the electrospun nanofiber. In some embodiments, one or more layers may include a layer of electrospun nanofibers below a coiled backbone, above it, or both below and above. These layers can possess complementary counterpart micro and/or nano features to those possessed by the coiled backbone. In some embodiments, the complementary counterpart micro and/or nano features are of a hook and loop configuration. In some embodiments, the complementary counterpart micro and/or nano features are of a tab and slot configuration, a ball and socket configuration, a tongue and groove configuration, or any other complementary structural configuration as aspects of the invention are not limited in this respect.

In some embodiments, aspects of the invention relate to an electrospun nanofiber tubular synthetic organ structure comprising a support structure (e.g., a coiled backbone) and/or perfusion pathway that possesses integrated micro and/or nano features that can anchor, attach, or bind to the electrospun nanofiber layer(s) it contacts. In some embodiments, the layers can include a layer of electrospun nanofibers on a first side of the support structure (e.g., the coiled backbone) and/or perfusion pathway, a second side of the support structure and/or perfusion pathway, or both. In some embodiments, the layers themselves act as permissive substrates for the anchoring, attachment, or binding of the coiled backbone and/or perfusion pathway they contact.

In some embodiments, aspects of the invention relate to an electrospun nanofiber tubular synthetic organ structure constructed using a single continuous electrospun nanofiber. In some embodiments, one or more separate support structures and/or perfusion pathways are incorporated into the organ structure. In some embodiments, the support structure (s) and/or perfusion pathway(s) are incorporated during electrospinning without stopping the electrospinning process (thereby maintaining a single continuous fiber which reduces the problem of delamination). In some embodiments, the electrospinning process is slowed rather than stopped. In some embodiments, the process is slowed using a concerted software control of two or more (e.g., all) adjustable electrospinning parameters. In some embodiments, the purpose of slowing the electrospinning process is to allow a software-controlled robot to place one or more support structures (e.g., backbone elements) and/or perfusion pathways onto a partially completed electrospun nanofiber tubular synthetic organ structure. In some embodiments, this placement is facilitated by using an encoder on the collector.

In some embodiments, the construction process is facilitated by using an electrospinning mandrel to tune the mechanical and biological properties of the electrospun nanofiber tubular synthetic organ structure, obviating the need for the insertion of one or more backbone elements.

In some embodiments, aspects of the invention relate to using simultaneous multi-fiber (e.g., 2-fiber) electro spinning with dense fibers (e.g., PET fibers) at the ribs and more elastic (e.g., PU or blended PET/PU) for spaces between the ribs (e.g., in the context of a scaffold having one or more support rib structures). In some embodiments, ribs are made by oscillating back and forth the angular rotation of the mandrel (e.g., approximately 270 degrees, however other angles may be used). In some embodiments, as many syringe nozzles as ribs (e.g., between 6 and 10, or more or less) may be used. In some embodiments, one or more nozzles can be moved stepwise along the longitudinal axis of a mandrel. In some embodiments, after a small mass of rib material is built up (e.g., between one hundredth and one fifth of total rib mass) for one or more ribs (e.g., all ribs), the posterior wall of the scaffold and the inter rib spaces can be covered in a layer of more elastic material (e.g., a blend of between 100% PU and 50% PU/50% PET). This process can be used to produce a scaffold made of a single mass of fibers, thereby reducing the delamination between layers of materials used in current scaffolds, while maintaining a radially strong but longitudinally flexible tracheal scaffold. Similarly, different patterns of deposition of one or more different fiber types can be used to create a network of channels to form one or more perfusion pathways within a scaffold during synthesis.

It should be appreciated that this technique also could be used for other organs, particularly tubular organs, for example the gastrointestinal tract, and for other organs requiring scaffolds with varying mechanical properties (e.g., hemi, bone, liver, or kidney) and/or perfusion pathways for delivering different materials (e.g., cells, nutrients, etc.) to promote cell growth and development during synthesis of a synthetic organ or tissue in a bioreactor, and/or to maintain cell survival during or after transplantation into a host subject In some embodiments, the same technique can be used with longitudinal ribs and/or associated perfusion pathways rather than radial ribs, for example for esophageal scaffold construction.

In some embodiments, delamination or other structural problems can be reduced by sewing a suture pattern into the scaffold (e.g., to maintain the integrity of structural supports and/or perfusion pathways that are associated with scaffold material).

In some embodiments, a scaffold is produced by providing layers of different percentages of two or more polymers. In some embodiments, different gradient percent changes are used. Accordingly, a continuous stream of fiber can be produced having varying concentrations (and different properties, e.g., different adhesive properties) to produce a continuous fiber with more binding and less delamination.

In some embodiments, a low concentration of solvent can be applied to the scaffold (e.g., sprayed over the scaffold or by soaking the scaffold in a low concentration solvent) to promote cross linking of fibers to structural supports (e.g., ribs). In some embodiments, the support structures (e.g., ribs) and/or perfusion pathways can have their surfaces modified. In some embodiments, the surfaces can be softened using solvent. In some embodiments, the surfaces can be produced with a rough or "hairy" surface (e.g., by spinning fibers onto ribs before assembly).

In some embodiments, a tethering structure (e.g., a ring or seal) can be applied to one or both ends of a tubular structure containing two or more layers of fibers (e.g., nanofibers) to prevent delamination.

In some embodiments, fibers that are not physically connected can be twisted. The twisting can be performed at set intervals. In some embodiments, the twisting can form a knot-like structure that can help hold separate fiber strands together.

In some embodiments, the ribs or other support structures and/or perfusion pathways can be molded, and fibers can be spun or woven around the support structures and/or perfusion pathways. FIG. 3, described in more detail below, illustrates a non-limiting example of a perfusion pathway that is coated with electrospun fibers. In some embodiments, the ribs or other support structures and/or perfusion pathways include small anchors (e.g., hair-like anchors) on their outer surfaces that help connect the structures to the electrospun or woven material.

In some embodiments, a heated mandrel can be used to melt (e.g., partially melt) one or more layers of fiber thereby promoting their connection by fusing them.

In some embodiments, two or more streams of fibers are provided. A first stream is continuous, and a second stream is intermittent (e.g., spitting small fibers).

In some embodiments, different layers and/or components of a synthetic scaffold are based on different materials as described herein.

Scaffold Structure Shape

It should be appreciated that aspects of the invention are useful for manufacturing any scaffold, for example, to include one or more different materials (for example to include one or more perfusion pathways). In some embodiments, methods and compositions described herein are also useful for enhancing the stability and/or structural integrity of any scaffold comprising two or more materials, for example scaffolds comprising electrospun fibers. It should also be appreciated that aspects of the disclosure provided scaffolds that are useful for producing synthetic organs and tissue structures, including both solid (e.g., liver, kidney, pancreas, muscle, cartilage, spleen) or hollow (e.g., stomach, bladder, intestines, trachea, lung, bone, vessels (e.g., blood vessels, lymphatic vessels), heart, vas deferens, urethra, fallopian tubes) organs and tissue structures. Examples described herein in the context of specified organs or tissue (e.g., kidney or tracheal scaffolds are not limiting unless otherwise indicated and illustrate configurations that can be used in scaffolds for different types of organs or tissues or portions thereof. As used herein, the term "hollow organ or tissue structure" refers to a organ or tissue structure that is a hollow tube or pouch or that includes a functional cavity. As used herein, the term "solid organ or tissue structure" refers to an organ or tissue structure that does not have substantially hollow or open interior spaces. In some embodiments, scaffolds are formed as tubular structures that can be seeded with cells to form tubular tissue regions (e.g., tracheal, bronchial, or other tubular regions for example, the bronchus). It should be appreciated that a tubular region can be a cylinder with a uniform diameter. However, in some embodiments, a tubular region can have any appropriate tubular shape (for example, including portions with different diameters along the length of the tubular region). A tubular region also can include a branch or a series of branches. In some embodiments, a tubular scaffold is produced having an opening at one end, both ends, or a plurality of ends (e.g., in the case of a branched scaffold). However, a tubular scaffold may be closed at one, both, or all ends, as aspects of the invention are not limited in this respect. It also should be appreciated that aspects of the invention may be used to produce scaffolds for any type or organ, including hollow and solid organs, as the invention is not limited in this respect. In some embodiments, aspects of the invention are useful to enhance the stability of scaffold or other structures that include two or more regions or layers of fibers (e.g., electrospun nanofibers) that are not physically connected.

It should be appreciated that aspects of the disclosure can be used to synthesize different scaffold components having different shapes and sizes (e.g., planar structures such as sheets of material, tubular structures, hollow structures, solid structures, more complex structures, or combinations thereof, any of which can have one or more dimensions ranging from about 1 mm to about 50 ems, for example, or smaller, intermediate, or larger sizes in different directions).

Support/Mandrel

In some embodiments, a scaffold (e.g., a scaffold having two or more layers) can be produced using a support (e.g., a solid or hollow support) on which the scaffold can be formed. For example, a support can be a mandrel, tube, or any other shaped support. It should be appreciated that the support can have any size or shape. However, in some embodiments, the size and shape of the support is designed to produce a scaffold that will support an artificial tissue of the same or similar size as the tissue being replaced or supplemented in a host (e.g., trachea or other airway portion, blood vessel, liver or kidney region, or other tissue or organ).

In some embodiments, a support structure (e.g., a mandrel) may be used to help shape or configure one or more components of a hybrid organ scaffold. In some embodiments, different support structures may be used for different types of material and/or for different manufacturing techniques (e.g., for printed material, for molded material, for polymerized material, for cast material, for electrospun material, etc.).

Scaffold Materials

In some embodiments, scaffolds comprise one or more types of natural material. In some embodiments, cartilage material, alginate, fibrin, chitosan, hyaluronic acid, basement membrane, extracellular material, collagens type I to III, V, and VI, proteoglycans, glycoproteins and/or glycosaminoglycans, and/or other natural materials are used. In some embodiments, the scaffold comprises a decellularized tissue (e.g., decellularized cartilage, skin or lung tissue).

In some embodiments, scaffolds comprise one or more types of molded or cast material.

In some embodiments, scaffolds are produced through solvent casting. In some embodiments, solvent casting involves dissolving a polymer in an organic solvent; particles, typically salts, are then added to the solution. In some embodiments, this polymer containing mixture is shaped into its final geometry by casting it in a three-dimensional mold to produce a scaffold. For example, in one kind of printing, the solvent then evaporates leaving behind a structure comprising the particles (e.g., salts) together with the polymer. In some embodiments, the composite material is then placed in a bath which dissolves the particles, leaving behind a porous scaffold.

In some embodiments, scaffolds comprise one or more types of biodegradable polymers. Example of biodegradable polymers include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Further examples of biodegradable polymers include synthetic polymers such as polymers of lactic acid and glycolic acid such as caprolactam, polycaprolactam, or poly(lactic-co-glycolic acid, polyanhydrides, poly(ortho) esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some embodiments, the biodegradable polymer is polyglycolic acid (PGA), polylactic acid (PLA), polyglycolic acid/polylactic acid copolymer (PLGA), polycaprolactone (PCL), polydioxanone, polycarbonate, or polyanhydride.

In some embodiments, scaffolds comprise one or more types of polymeric material. In some embodiments, one or more poly(-hydroxy esters), for example, PGA, PLA, and/or PLGA and/or other polymers are used. In some embodiments, scaffolds comprise biodegradable polymers. In some embodiments, biodegradable polymers are non-toxic, capable of maintaining sufficient mechanical integrity until degraded or during degradation, and/or capable of controlled rates of degradation. In some embodiments, a biodegradable polymer is inert (e.g., does not illicit and immune response). In some embodiments, the products of degradation of a polymer are non-toxic. In some embodiments, degradation rates of a polymer are influenced by percent crystallinity, molecular weight of constituent polymers, hydrophobicity, etc. The degradation rate may depend on the location in the body, in some embodiments.

In some embodiment, the mold in which the scaffold is cast is composed of a metal (e.g., stainless steel) or a polymer (e.g., an acrylic polymer, e.g., polymethylmethacrylate). In some embodiments, materials, such as biodegradable polymers may be printed to form a scaffold.

Fibers

In some embodiments, scaffolds comprise one or more types of fiber (e.g., nanofibers). In some embodiments, scaffolds comprise one or more natural fibers, one or more synthetic fibers, one or more polymers, or any combination thereof. It should be appreciated that different material (e.g., different fibers) can be used in methods and compositions described herein. In some embodiments, the material is biocompatible so that it can support cell growth. In some embodiments, the material is permanent (e.g., PET), semi-permanent (e.g., it persists for several years after implantation into the host, or rapidly degradable (e.g., it is resorbed within several months after implantation into the host).

In some embodiments, the scaffold contains or consists of electrospun material (e.g., nanofibers). In some embodiments, the electrospun material contains or consists of PET (polyethylene terephthalate (sometimes written poly(ethylene terephthalate)). PET is a thermoplastic polymer resin of the polyester family. PET consists of polymerized units of the monomer ethylene terephthalate, with repeating $C_{10}H_8O_4$ units. Depending on its processing and thermal history, polyethylene terephthalate may exist both as an amorphous (transparent) and as a semi-crystalline polymer. The semicrystalline material might appear transparent (particle size<500 nm) or opaque and white (particle size up to a few microns) depending on its crystal structure and particle size. Its monomer (bis-β-hydroxyterephthalate) can be synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with water as the byproduct. In some embodiments, the electrospun material contains or consists of polyurethane (PU). In some embodiments, the electrospun material contains or consists of PET and PU.

In some embodiments, the artificial scaffold may consist of or include one or more of any of the following materials: elastic polymers (e.g., one or more polyurethanes (PU), for example polycarbonates and/or polyesters), acrylamide polymers, Nylon, resorbable materials (e.g., PLGA, PLA, PGA, PCL), synthetic or natural materials (e.g., silk, elastin, collagen, carbon, gelatin, chitosan, hyaluronic acid, etc.) or any combination thereof. In some embodiments, the scaffold may consist of or include addition polymer and/or condensation polymer materials such as polyolefin, polyacetal, polyamide, polyester, cellulose ether and ester, polyalkylene sulfide, polyarylene oxide, polysulfone, modified polysulfone polymers and mixtures thereof. In some embodiments, the scaffold may consist of or include polyethylene, polypropylene, poly(vinylchloride), polymethylmethacrylate (and other acrylic resins), polystyrene, and copolymers thereof (including ABA type block copolymers), poly(vinylidene flumide), poly(vinylidene chloride), polyvinylalcohol in various degrees of hydrolysis (e.g., 87% to 99.5%) in cross-linked and non-cross-linked forms. In some embodiments, the scaffold may consist of or include block copolymers. In some embodiments, addition polymers like polyvinylidene fluoride, syndiotactic polystyrene, copolymer of vinylidene fluoride and hexafluoropropylene, polyvinyl alcohol, polyvinyl acetate, amorphous addition polymers, such as poly(acrylonitrile) and its copolymers with acrylic acid and methacrylates, polystyrene, poly(vinyl chloride) and its various copolymers, poly(methyl methacrylate) and its various copolymers, and PET (polyethylene terephthalate (sometimes written poly(ethylene terephthalate))) can be solution spun or electrospun and combined with any other material disclosed herein to produce a scaffold. In some embodiments, highly crystalline polymers like polyethylene and polypropylene may be solution spun or combined with any other material disclosed herein to produce a scaffold.
Electrospinning In some embodiments, aspects of the invention relate to structures or components thereof that are produced via electrospinning. Methods of electrospinning polymers are known in the art (see, e.g. (Doshi and Reneker, Electrospinning process and application of electrospun fibers. J Electrostat. 1995; 35:151-60; Reneker D H, Chun I. Nanometer diameter fibers of polymer produced by electrospinning. Nanotechnology. 1996; 7:216-23; Dzenis Y. Spinning continuous fibers for nanotechnology. Science. 2004; 304:1917-19; or Vasita and Katti. Nanofibers and their applications in tissue engineering. Int J. Nanomedicine. 2006; 1 (1): 15-30). Electrospinning is a versatile technique that can be used to produce either randomly oriented or aligned fibers with essentially any chemistry and diameters ranging from nm scale (e.g., around 15 nm) to micron scale (e.g., around 10 microns).

It should be appreciated that synthetic scaffolds described herein can be used to produce engineered organs or tissue that can be implanted into a subject in need thereof or used ex vivo. In some embodiments, perfused structures described herein support cell and tissue growth for more than one month (e.g., more than 2, 3, 4, 5, 6, 7, 8, 9, 10, 11 months or more than one year). Perfusion pathways described herein can be used during growth and development of an engineered organ or tissue and/or during use of the organ or tissue. In some embodiments, one or more inlets and/or outlets of a perfusion pathway are connected to components of a pump, syringe, or other fluid handling device. In some embodiments, one or more inlets and/or outlets of a perfusion pathway are connected to the vasculature of a subject to provide for blood flow through the organ or tissue after transplantation.

It should be appreciated that techniques described herein may be used to provide a synthetic scaffold for any tissue or organ (including, airways, lungs, blood vessels, kidneys, livers, hearts, pancreas, bladder etc.). It also should be appreciated that synthetic scaffolds may be used for human or other tissue or organ engineering applications.

These and other aspects are illustrated by the following non-limiting examples.

EXAMPLES

Figure 2:
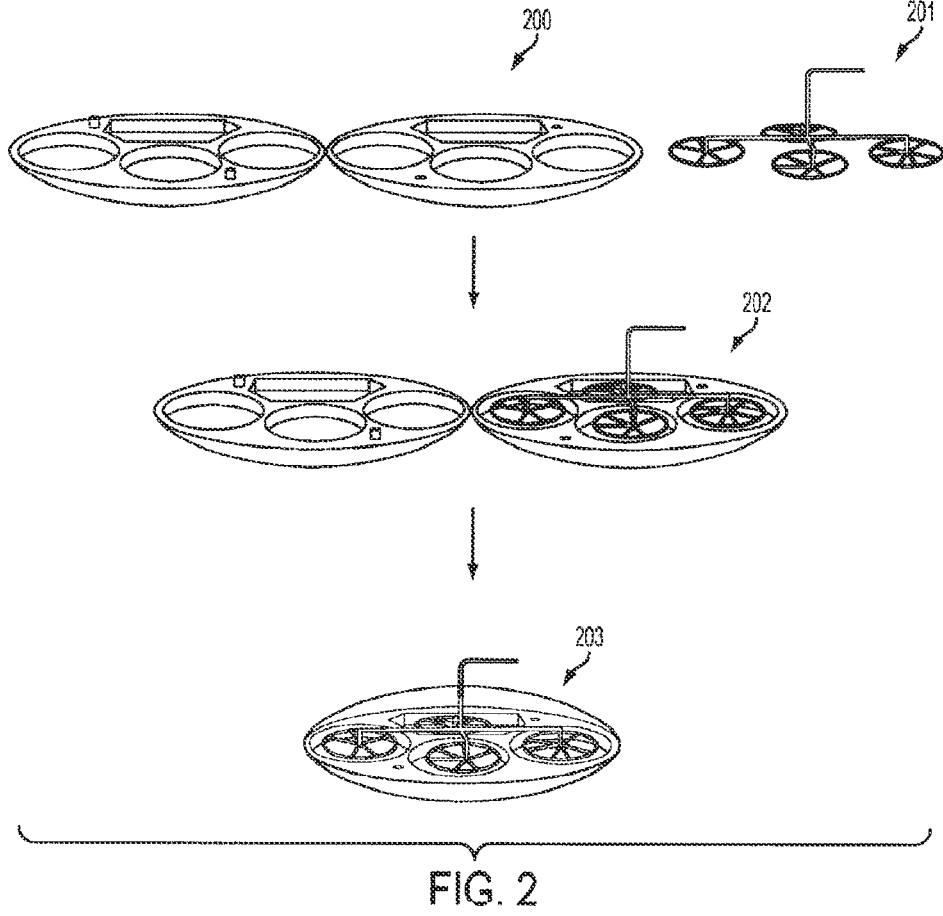
FIG. 2 depicts a non-limiting example of an organ scaffold (e.g., a kidney scaffold)

A non-limiting example of an organ scaffold (e.g., a kidney scaffold) is illustrated in FIG. 2. In FIG. 2, the top panel illustrates an example of a printed structural component 200 that is provided in the form of two parts (e.g., two half shells) that can be assembled to form a single external structure that encloses an internal space. In this example, each printed element defines part of an external shell and several internal spaces. Once assembled, the external structure provides, for example, a protective shell or outer coating for a synthetic organ, (e.g., a synthetic kidney or liver). The first panel also illustrates an example of a molded perfusion component 201. This nonlimiting example includes conduits (e.g., of different diameters) connected to form a pathway. In some embodiments, the networks (e.g., those at the lower end of the pathway) can be covered in a material (e.g., an electrospun material) that can support cell growth. The second panel 202 illustrates the molded perfusion component inserted into one side of the printed structural component. The third panel 203 illustrates an assembly of the perfusion component within the internal space formed by both parts structural component attached together. In some embodiments, scaffold material that can support cells growth (e.g., micro or nano fibers, for example electrospun fibers) can be included in one or more of the internal spaces (e.g., in the form of a matrix of fibers). In some embodiments, one or more of the perfusion components are embedded within a scaffold material (e.g., an electrospun material) in one or more of the internal spaces. The perfusion components can be used to deliver cells and/or provide nutrients, oxygen, and/or other materials to support cell growth within the one or more internal spaces. In some embodiments, cells are deposited into one or more of the cavities or internal spaces (for example without using the perfusion pathway) prior to enclosing the internal space between the two outer shell components.

It should be appreciated that different configuration of outer shell components can be used. In some embodiments, more than two pieces are assembled to provide the support and internal spaces for cellular matrices and/or perfusion networks. In some embodiments, the pieces are not equal in size (e.g., the do not represent two halves of a shell). For example, one or more pieces can form the cavities and/or other spaces into which the cell matrices and or perfusion pathway components can be placed (e.g., along with one or more cell types). One or more further pieces can be used as a lid to enclose these components once they are in place. However, it should be appreciated that one or more orifices may be included in the outer shell (or be formed at the junction between two or more pieces of an outer shell) to allow one or more channels of a perfusion pathway to connect the internal space to the external space as illustrated in FIG. 2.

It should be appreciated that the external structure and/or perfusion component can be synthesized using any technique described herein, including but not limited to molding, electrospinning, printing, casting, extruding, or other technique or combination thereof as aspects of the disclosure are not limited in this respect.

It also should be understood that the configuration illustrated in FIG. 2 is non-limiting. Other configurations can be synthesized wherein an outer material (e.g., shell) can include one or more cavities or internal spaces within which cells can be grown (e.g., on a scaffold of biocompatible material, for example a scaffold of fibers). Accordingly, one or more cavities or internal spaces can include a biocompatible scaffold that is synthesized to support cell growth. In some embodiments, a perfusion pathway is included and can reach one or more cavities or internal spaces. In some embodiments, a network of perfusion conduits can be embedded within a biocompatible scaffold or matrix within one or more cavities or internal spaces. Each network can be connected together or independently to one or more inlets and/or outlets to reservoirs and fluid delivery systems (for example to deliver and remove material to support cell growth as described herein).

A non-limiting example of organ perfusion channels is illustrated in FIGS. 3A-3F. Organ perfusion channels can be used for hollow organs and/or solid organs. In some embodiments, polyglycolic acid tubes or other absorbable material may be used. In some embodiments, electrospun material may be used. In some embodiments, perfusion channels maybe structural and/or vascular in nature, providing suitable support, rigidity and/or flexibility to an organ as well as serving as a vascular conduit to transport and distribute nutrients, drugs, fluids, and/or gases to the internal structures of an organ to promote nutrition, angiogenesis, and/or other functions. FIG. 3A depicts a perfusion chamber having a primary passage 306 fluidically connected with a set of branching passages 300. FIG. 3B depicts a perfusion chamber having a perfusion pathway having complex network of passages 301 of various sizes and orientations. FIG. 3C depicts an end view of a perfusion pathway having an branching passage 300 connected to a primary passage 306 embedded within a surrounding material 307. FIG. 3D depicts a perfusion pathway having a primary passage fluidically connected with a set of branching passages 300, in which a set of ribs 302 overlay the branching passages and in which a perfusion media 303 leaks out into a surrounding space or material. FIG. 3E depicts a perfusion chamber having a primary passage fluidically connected with a set of branching passages 300, in which a set of ribs and electrospun fibers 304 overlay the branching passages. FIG. 3F depicts a perfusion chamber having a primary passage, in which a set of ribs 302 overlay the branching passages and in which a perfusion media leaks 303 out orifices 305 in the primary passage into a surrounding space or material.

Figure 4:
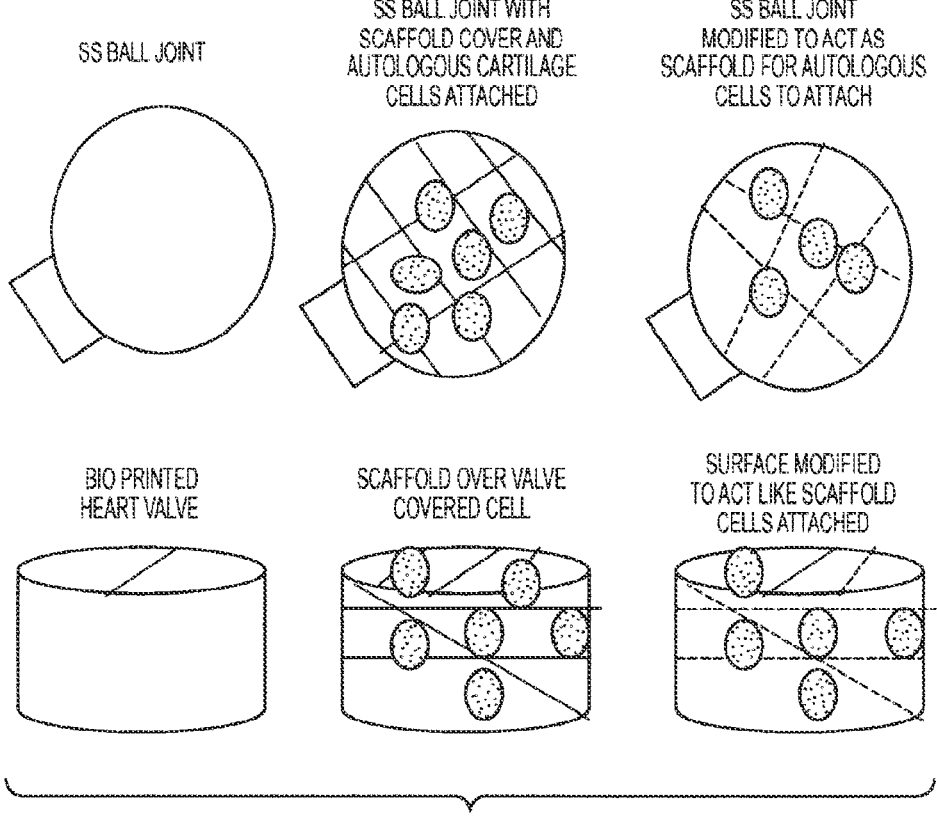
FIG. 4 depicts a non-limiting example of a cell-compatible material covering an artificial structure.

A non-limiting example of a cell-compatible material covering an artificial structure is illustrated in FIG. 4 that illustrates surface coatings and/or modifications of a stainless steel (SS) ball joint. Material that can promote cell growth (e.g., porous, for example electrospun material) can be used as a covering to promote cell deposition (e.g., for autologous cell deposition). However, FIG. 4 also illustrates that the surface of the ball joint can be modified (e.g., alone or in addition to being coated) to promote cell adhesion. This can be useful to provide additional biological functions and/or prevent or reduce immune rejection of an artificial material. In some embodiments, this can help integrate one or more portions of the ball joint into a site of implantation (e.g., in a bone or cartilage context). It should be appreciated that one or more scaffold components can be surface-coated and/or modified to promote cellularization (for example in the bioreactor and/or after implantation into a host subject).

Figure 5:
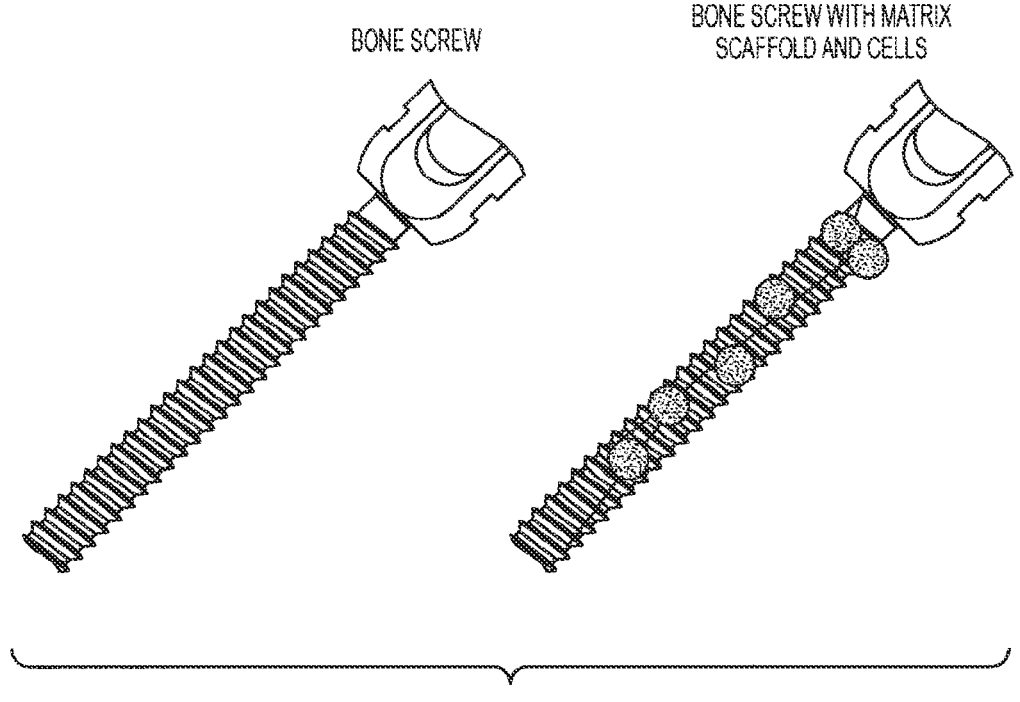
FIG. 5 depicts non-limiting examples of artificial devices covered (e.g., partially or completely) with one or more different types of material that promotes cell growth.

FIG. 5 provides additional non-limiting examples of artificial devices that can be covered (e.g., partially or completely) with one or more different types of material that promotes cell growth. In some embodiments, the devices can have different patterns and/or types of coating to establish different surface characteristics. In some embodiments, the device can be coated with materials (e.g., biopolymers) that promote cell attachment and growth. In some embodiments, the device can be coated with materials (e.g., biopolymers) in certain regions of the device to promote cell attachment and growth at the certain regions. In some embodiments, a perfusion pathway can be present on a device and optionally be coated with a synthetic scaffold, in which case the perfusion pathway provides passages that facilitate delivery of nutrients and/or removal of cellular waste products from cells present on a surrounding scaffold.

Figure 6A:
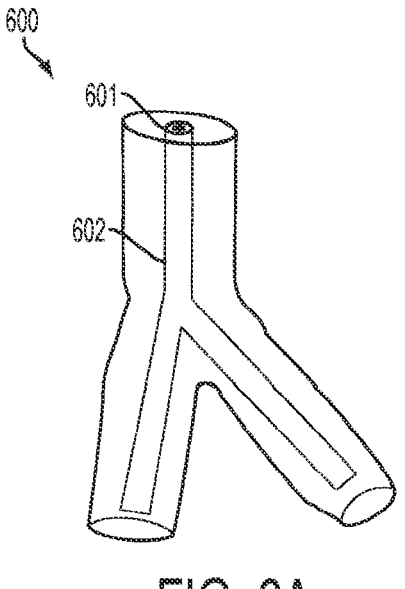
FIG. 6A-6B depict a non-limiting example of fluid delivery to a tracheal scaffold.
Figure 6B:
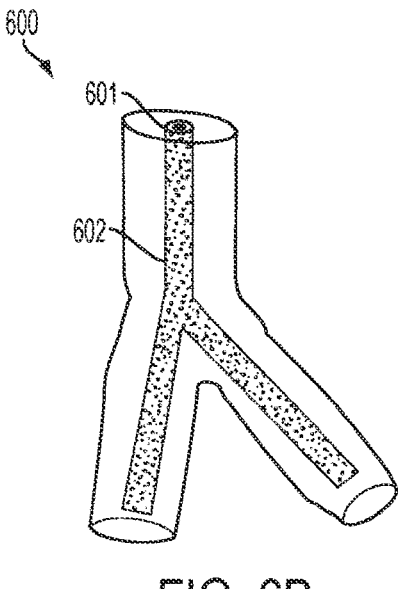

FIG. 6 illustrates a non-limiting embodiment for the injection of fluid (e.g., fluid containing cell growth factors or other tissue promoting factors, for example a vascularization fluid and/or a cell growth fluid) into a perfusion pathway (e.g., channel or network) within a tracheal scaffold. The perfusion channel or network can be provided and attached to the tracheal scaffold (e.g., by electrospinning) in some embodiments. In some embodiments, the perfusion channel or network itself is electrospun. In some embodiments, the perfusion channel or network is printed, molded, cast, etched, or otherwise produced within the tracheal scaffold. In some embodiments, two or more perfusion channels or networks are provided. In some embodiments, different fluids are injected into each of the two or more channels or networks. In some embodiments, the same fluid is injected into two or more channels or networks (e.g., to facilitate or promote even distribution throughout the scaffold). In some embodiments, the patterns of the channels or networks is different for different fluids that are being injected (e.g., to promote different types of tissue growth in different regions of the tracheal implant, for example, to promote cartilage, muscle, blood, nerve, and/or other cell development in separate or different but overlapping regions of the organ. FIG. 6A illustrates a top-view of a tracheal scaffold showing a branched perfusion pathway that can be placed on the surface of the scaffold or incorporated within the scaffold. The perfusion pathway can be connected (e.g., via fluid connection) to a fluid delivery system (e.g., a pump, syringe, or other system that can generate a pressure to drive fluid flow through the perfusion pathway) via a perfusion inlet. FIG. 6B illustrates fluid filling the internal channel of the perfusion pathway. Fluid and/or material within the fluid (e.g., cells, nutrients, growth factors, etc.) can be delivered along the length of the perfusion pathway and/or to specific regions of the perfusion pathway by including one or more openings and/or by incorporating regions of the wall of the perfusion channel having different permeabilities and/or porosities. Non-limiting examples are illustrated in more detail in FIG. 7.

In some embodiments, fluid may be injected into the scaffold prior to cellularization. In addition, or alternatively, fluid may be injected after cellularization but before the structure is implanted in a host subject. In some embodiments, fluid can be injected after implantation.

In some embodiments, a perfusion pathway may have one or more inlet valves and/or one or more outlet valves (e.g., fitted within inlet or outlet conduits) that control flow of a perfusion fluid through the pathway. With reference to FIG. 1, for example, suitable valves may be configured within inlet 103 and outlet 104. Suitable valves include ball valves, gate valves, pressure control valves, flow control valves, etc. Valves and other system components, including fluid transfer device, such as pumps, may be configured with suitable instrumentation for automated control of system conditions that are appropriate for particular applications. In some embodiments, a perfusion pathway may include a relief valves or other components to allow the fluid to be injected without causing a pressure build-up within the pathway.

Figure 8:
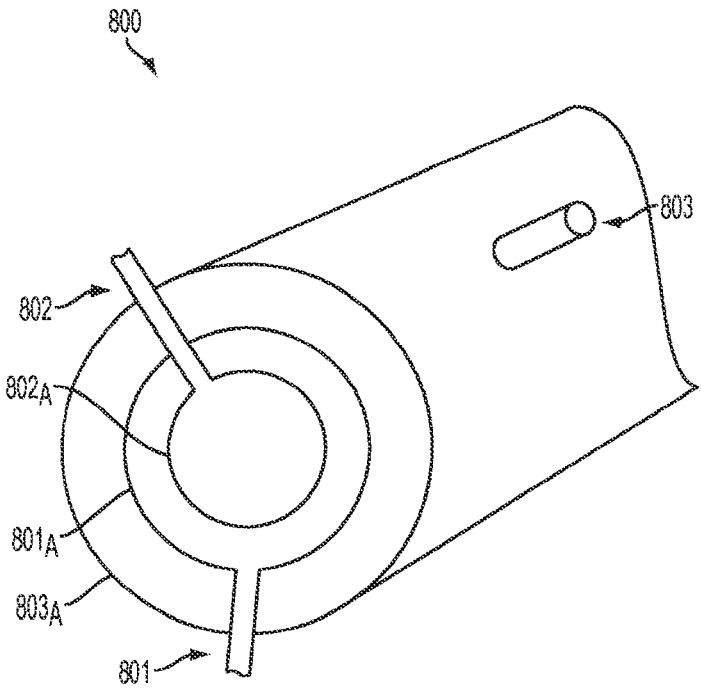
FIG. 8. depicts a further non-limiting example of a synthetic delivery system that can be used to deliver material to predefined positions on or in a synthetic organ or tissue.

FIGS. 7 and 8 illustrate non-limiting embodiments of a synthetic delivery system (e.g., an internal or external perfusion system) that can be used to deliver material (e.g., hormones, growth factors, cells, nutrients, or other material) to predefined positions on or in a synthetic organ or tissue. FIG. 7A illustrates an isometric view of an embodiment where material 703 is distributed along the length of a longitudinal perfusion system 702 that can be positioned on the surface of a tubular synthetic organ or tissue or that can be incorporated within (e.g., internal to) a tubular synthetic organ or tissue or scaffold 700. A perfusion channel 702 is shown integrated into the wall of the scaffold. In operation, perfusion channel 702 is connected to a material delivery system (not shown). The material delivery system can be a syringe, pump, or other system that generates a pressure to drive material (e.g., in a fluid as described herein). Material 703 is illustrated coming out through openings 705 that are distributed along the length of the longitudinal perfusion channel 702. It should be appreciated that the openings can be of any suitable shape or size. The opening are orifices on the surface of the perfusion channel 702 that provide fluid communication between the internal volume of the channel and the surrounding space or material. It also should be appreciated that in some embodiments the walls of the perfusion channel are sufficiently permeable or porous to allow the material to leave the channel into the surrounding space along the length of the channel without requiring the presence of openings through the side walls. FIG. 7B illustrates an embodiment where material is targeted to a particular region in addition to being distributed along the length of an internal perfusion system. FIG. 7B illustrates a side channel 704 branching off perfusion channel 702. Channel 704 is illustrated with an open end through which material can be deposited to a particular location. It should be appreciated that a perfusion channel described herein can have a plurality of branches of different sizes and lengths to deliver material to different regions of a scaffold. It also should be appreciated that in some embodiments one or more branches have an open end as illustrated in FIG. 7 that terminate within the scaffold. In some embodiments, branches have closed ends that terminate within the scaffold. In some embodiments, branches do not terminate within the scaffold but are connected to an outlet pathway (e.g., via a branched pathway leading to one or more outlet conduits). In some embodiments, branches have permeable, semipermeable, or porous side walls, and/or have one or more openings in their side walls.

The scaffold as disclosed herein such as scaffold 701 can also include a coating such coating material 706 that is configured to promote cellularization that overlays at least a portion of the outer surface of the structure to assist and promote cellular adhesion and cell growth. The coating 706 is interposed between the surface of the scaffold 701 and one or more types of cells 707 seeded on the scaffold.

FIG. 8 is an isometric view illustrating several internal delivery pathways 801, 802, and 803 in an organ or tissue scaffold 800 that can be used to deliver material to concentric regions 801A, 802A, and 803A of a tubular synthetic organ or tissue. It should be appreciated that each pathway can be connected to a fluid delivery device (e.g., syringe, pump, etc.).

It should be appreciated that a plurality of different internal systems (e.g., interconnected or not) may be used to distribute different materials to different regions of a synthetic organ or tissue. Accordingly, different target regions may be independently addressable using separate internal delivery systems. In some embodiments, the internal delivery system is biodegradable and may be used, for example, during a particular period (e.g., during initial growth and development of the synthetic organ). However, in some embodiments, one or more internal delivery systems can be stable. These may be useful, for example, to maintain the ability to deliver one or more materials to predetermined regions of a synthetic organ or tissue at any time (e.g., including after implantation).

It should be appreciated that different configurations can be used for different tissue and organ types. It should be appreciated that these principles may be applied to other organ or tissue scaffolds.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein.

It is therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with noB present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements The following publications are incorporated herein by reference in their entireties for all purposes: International Patent Application Publication Serial Number WO2013 1163358, which published on a Oct. 31, 2013 and is entitled, ENGINEERED TISSUE SCAFFOLDS AND SUPPORTS THEREOF; International Patent Application Publication Serial Number WO 2011/034627, which published on a Mar. 24, 2011 and is entitled, METHODS AND APPARATUS FOR INTRODUCING CELLS AT A TISSUE SITE; International Patent Application Publication Serial Number WO 20111062621, which published on a May 26, 2011 and is entitled, BIOREACTORS, SYSTEMS, AND METHODS FOR PRODUCING AND/OR ANALYZING ORGANS; International Patent Application Publication Serial Number WO 2013/110021, which published on a Jul. 25, 2013 and is entitled, METHOD FOR EVALUATING TISSUE INJURIES; International Patent Application Publication Serial Number WO 20131155488, which published on a Oct. 17, 2013 and is entitled, ELASTIC SCAFFOLDS FOR TISSUE GROWTH; International Patent Application Publication Serial Number WO 2014/004746, which published on a Jan. 3, 2014 and is entitled, METHODS AND COMPOSITIONS FOR PROMOTING THE STRUCTURAL INTEGRITY OF SCAFFOLDS FOR TISSUE ENGINEERING; and International Patent Application Serial Number PCT/US13/52437, which was filed on Jul. 28, 2013 and entitled ANALYTICAL METHODS.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method of producing an implantable synthetic scaffold for use in a hollow tubular organ, the method comprising:

assembling a synthetic scaffold using a first synthetic material for a first structural component configured as a hollow tubular member having a cylindrical wall and at least one surface and a second material for a second structural component, wherein the second material is selected from synthetic material, natural material, and mixtures thereof, wherein the first structural component or the second structural component can simulate growth by expanding to a cue or in response to cellular or tissue growth and wherein the first synthetic material for the first structural component is printed, molded, cast, polymerized, or electrospun, and wherein the second structural component is configured as a perfusion pathway within the cylindrical wall of the hollow tubular member; and seeding one or more cell types on the at least one surface of the hollow tubular member prior to implantation in a body of a subject, wherein the synthetic scaffold implantable in the hollow tubular organ has a size and shape that is similar to the hollow tubular organ and wherein the perfusion pathway formed by the second structural component has a first end, a second end, and a plurality of branches that extend from the perfusion pathway and are disposed between the first end and the second end, wherein the first end of the perfusion pathway is releasably connectable to a bioreactor, and the second end of the perfusion pathway is proximate to the one or more cell types seeded on the at least one surface of the hollow tubular member, and wherein the plurality of branches are configured to deliver a perfusion fluid to the synthetic scaffold and/or tissue of the subject and extend through the tissue of the subject when inserted in the subject so that cellularization, cell viability, or cell growth is improved when the synthetic scaffold is implanted in the subject.

2. The method of claim 1, wherein the first synthetic material is electrospun, and wherein a portion of the perfusion pathway is configured as a cylindrical conduit extending longitudinally along a portion of the hollow tubular member.

3. The method of claim 1, the perfusion pathway comprises isotropically oriented passages or anistropically oriented passages, each having an inlet and an outlet and a wall structure interposed between the inlet and the outlet.

4. The method of claim 3, wherein the second material is printed, molded, cast, polymerized, or electrospun, and wherein the first synthetic material or the second material is selected from a group consisting of polyethylene terephthalate, polyurethane and mixtures thereof either alone or in combination with one or more of acrylamide polymers, polyamide, poly(lactic-co-glycolic acid), polylactic acid, polyglycolic acid, polycaprolactam.

5. The method of claim 1 wherein at least one of the first synthetic material or the second structural components simulate cell growth by expanding over time.

* * * * *